US011554013B2

(12) United States Patent
Lee et al.

(10) Patent No.: US 11,554,013 B2
(45) Date of Patent: Jan. 17, 2023

(54) DELIVERY SYSTEMS FOR PROSTHETIC HEART VALVE

(71) Applicant: Edwards Lifesciences Corporation, Irvine, CA (US)

(72) Inventors: Walter Lee, Irvine, CA (US); Mark Dehdashtian, Irvine, CA (US); Teodoro S. Jimenez, Irvine, CA (US); Gilbert S. Leung, Irvine, CA (US); Bryan A. Janish, Huntington Beach, CA (US); Michael G. Valdez, Riverside, CA (US); Tram Ngoc Nguyen, Santa Ana, CA (US); Timothy C. Ulrich, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 785 days.

(21) Appl. No.: 16/220,385

(22) Filed: Dec. 14, 2018

(65) Prior Publication Data
US 2019/0125532 A1 May 2, 2019

Related U.S. Application Data

(60) Continuation of application No. 14/827,172, filed on Aug. 14, 2015, now Pat. No. 10,179,047, which is a
(Continued)

(51) Int. Cl.
*A61F 2/95* (2013.01)
*A61F 2/24* (2006.01)
(Continued)

(52) U.S. Cl.
CPC ............ *A61F 2/2433* (2013.01); *A61F 2/958* (2013.01); *A61F 2/484* (2021.08); *A61F 2/9517* (2020.05);
(Continued)

(58) Field of Classification Search
CPC ........ A61F 2/2433; A61F 2/958; A61F 2/484; A61F 2/9517; A61F 2250/0021;
(Continued)

(56) References Cited

U.S. PATENT DOCUMENTS 3,409,013 A 11/1968 Berry
3,472,230 A 10/1969 Fogarty
(Continued)

FOREIGN PATENT DOCUMENTS

DE 2246526 A1 3/1973
DE 0144167 C 6/1985
(Continued)

OTHER PUBLICATIONS

/Joel B. German/.
(Continued)

*Primary Examiner* — Erich G Herbermann
(74) *Attorney, Agent, or Firm* — Klarquist Sparkman, LLP; Joel B. German

(57) ABSTRACT

Described herein are systems and methods from delivering prosthetic devices, such as prosthetic heart valves, through the body and into the heart for implantation therein. The prosthetic devices delivered with the delivery systems disclosed herein are, for example, radially expandable from a radially compressed state mounted on the delivery system to a radially expanded state for implantation using an inflatable balloon of the delivery system. Exemplary delivery routes through the body and into the heart include transfemoral routes, transapical routes, and transaortic routes, among others.

19 Claims, 19 Drawing Sheets

Related U.S. Application Data division of application No. 13/559,395, filed on Jul. 26, 2012, now Pat. No. 9,119,716.

(60) Provisional application No. 61/512,328, filed on Jul. 27, 2011.

(51) Int. Cl.
  *A61F 2/958* (2013.01)
  *A61M 25/10* (2013.01)
  *A61F 2/48* (2006.01)

(52) U.S. Cl.
  CPC ............... *A61F 2002/9586* (2013.01); *A61F 2250/0003* (2013.01); *A61F 2250/0021* (2013.01); *A61M 25/1002* (2013.01); *A61M 25/10184* (2013.11); *A61M 2025/1013* (2013.01); *A61M 2025/1084* (2013.01)

(58) Field of Classification Search
  CPC ...... A61F 2250/0003; A61F 2002/9586; A61F 2/95; A61F 2002/9511; A61F 2250/1013; A61F 2250/1084; A61M 25/10184; A61M 25/1002; A61M 2025/1013; A61M 2025/1084
  See application file for complete search history.

(56) References Cited

U.S. PATENT DOCUMENTS

| | | |
|---|---|---|
| 3,548,417 A | 12/1970 | Kisher |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,797,901 A | 1/1989 | Goerne et al. |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,955,895 A | 9/1990 | Sugiyama et al. |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,108,370 A | 4/1992 | Walinsky |
| 5,152,771 A | 10/1992 | Sabbaghian et al. |
| 5,163,953 A | 11/1992 | Vince |
| 5,167,628 A | 12/1992 | Boyles |
| 5,176,698 A | 1/1993 | Burns et al. |
| 5,192,297 A | 3/1993 | Hull |
| 5,232,446 A | 8/1993 | Arney |
| 5,266,073 A | 11/1993 | Wall |
| 5,282,847 A | 2/1994 | Trescony et al. |
| 5,295,958 A | 3/1994 | Shturman |
| 5,304,198 A | 4/1994 | Samson |
| 5,332,402 A | 7/1994 | Teitelbaum |
| 5,358,487 A | 10/1994 | Miller |
| 5,358,496 A | 10/1994 | Ortiz et al. |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,470,313 A | 11/1995 | Crocker et al. |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,599,305 A | 2/1997 | Hermann et al. |
| 5,607,464 A | 3/1997 | Trescony et al. |
| 5,609,626 A | 3/1997 | Quijano et al. |
| 5,628,792 A | 5/1997 | Lentell |
| 5,632,760 A | 5/1997 | Sheiban et al. |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,769,814 A | 6/1998 | Wijay |
| 5,776,099 A | 7/1998 | Tremulis |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,908,405 A | 6/1999 | Imran et al. |
| 5,925,063 A | 7/1999 | Khosravi |
| 5,957,949 A | 9/1999 | Leonhardt et al. |
| 5,968,068 A | 10/1999 | Dehdashtian et al. |
| 5,968,069 A | 10/1999 | Dusbabek et al. |
| 6,027,510 A | 2/2000 | Alt |
| 6,027,525 A | 2/2000 | Suh et al. |
| 6,033,381 A | 3/2000 | Kontos |
| 6,042,607 A | 3/2000 | Williamson, IV et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |

(56) References Cited

U.S. PATENT DOCUMENTS

| | | |
|---|---|---|
| 6,231,602 B1 | 5/2001 | Carpentier et al. |
| 6,235,050 B1 | 5/2001 | Quiachon et al. |
| 6,245,040 B1 | 6/2001 | Inderbitzen et al. |
| 6,245,102 B1 | 6/2001 | Jayaraman |
| 6,264,683 B1 | 7/2001 | Stack et al. |
| 6,299,637 B1 | 10/2001 | Shaolian et al. |
| 6,302,906 B1 | 10/2001 | Goicoechea et al. |
| 6,350,277 B1 | 2/2002 | Kocur |
| 6,352,547 B1 | 3/2002 | Brown et al. |
| 6,379,372 B1 | 4/2002 | Dehdashtian et al. |
| 6,425,916 B1 | 7/2002 | Garrison et al. |
| 6,440,164 B1 | 8/2002 | DiMatteo et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,514,228 B1 | 2/2003 | Hamilton et al. |
| 6,527,979 B2 | 3/2003 | Constantz |
| 6,569,196 B1 | 5/2003 | Vesely |
| 6,579,305 B1 | 6/2003 | Lashinski |
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |
| 6,733,525 B2 | 5/2004 | Yang et al. |
| 6,764,504 B2 | 7/2004 | Wang et al. |
| 6,767,362 B2 | 7/2004 | Schreck |
| 6,769,161 B2 | 8/2004 | Brown et al. |
| 6,783,542 B2 | 8/2004 | Eidenschink |
| 6,830,584 B1 | 12/2004 | Seguin |
| 6,872,215 B2 | 3/2005 | Crocker et al. |
| 6,878,162 B2 | 4/2005 | Bales et al. |
| 6,893,460 B2 | 5/2005 | Spenser et al. |
| 6,908,481 B2 | 6/2005 | Cribier |
| 6,936,067 B2 | 8/2005 | Buchanan |
| 7,018,406 B2 | 3/2006 | Seguin et al. |
| 7,018,408 B2 | 3/2006 | Bailey et al. |
| 7,052,510 B1 | 5/2006 | Richter |
| 7,096,554 B2 | 8/2006 | Austin et al. |
| 7,225,518 B2 | 6/2007 | Eidenschink et al. |
| 7,276,078 B2 | 10/2007 | Spenser et al. |
| 7,276,084 B2 | 10/2007 | Yang et al. |
| 7,318,278 B2 | 1/2008 | Zhang et al. |
| 7,374,571 B2 | 5/2008 | Pease et al. |
| 7,381,210 B2 | 6/2008 | Zarbatany et al. |
| 7,393,360 B2 | 7/2008 | Spenser et al. |
| 7,462,191 B2 | 12/2008 | Spenser et al. |
| 7,510,575 B2 | 3/2009 | Spenser et al. |
| 7,563,280 B2 | 7/2009 | Anderson et al. |
| 7,579,381 B2 | 8/2009 | Dove |
| 7,585,321 B2 | 9/2009 | Cribier |
| 7,594,926 B2 | 9/2009 | Linder et al. |
| 7,597,709 B2 | 10/2009 | Goodin |
| 7,618,446 B2 | 11/2009 | Andersen et al. |
| 7,618,447 B2 | 11/2009 | Case et al. |
| 7,621,948 B2 | 11/2009 | Herrmann et al. |
| 7,655,034 B2 | 2/2010 | Mitchell et al. |
| 7,785,366 B2 | 8/2010 | Maurer et al. |
| 7,959,661 B2 | 6/2011 | Hijlkema et al. |
| 7,959,672 B2 | 6/2011 | Salahieh et al. |
| 7,993,394 B2 | 8/2011 | Hariton et al. |
| 8,007,992 B2 | 8/2011 | Tian et al. |
| 8,029,556 B2 | 10/2011 | Rowe |
| 8,167,932 B2 | 5/2012 | Bourang |
| 8,221,349 B2 | 7/2012 | Auyoung et al. |
| 8,291,570 B2 | 10/2012 | Eidenschink et al. |
| RE43,882 E | 12/2012 | Hopkins et al. |
| 8,407,380 B2 | 3/2013 | Matsunaga et al. |
| 8,449,606 B2 | 5/2013 | Eliasen et al. |
| 8,454,685 B2 | 6/2013 | Hariton et al. |
| 8,568,472 B2 | 10/2013 | Marchand et al. |
| 8,652,203 B2 | 2/2014 | Quadri et al. |
| 8,747,463 B2 | 6/2014 | Fogarty et al. |
| 8,795,346 B2 * | 8/2014 | Alkhatib ................ A61F 2/958 623/1.11 |
| 9,078,781 B2 | 7/2015 | Ryan et al. |
| 9,119,716 B2 | 9/2015 | Lee et al. |
| 9,339,384 B2 | 5/2016 | Tran et al. |
| 9,795,477 B2 | 10/2017 | Tran et al. |
| 10,179,047 B2 | 1/2019 | Lee et al. |
| 2001/0007082 A1 | 7/2001 | Dusbabek et al. |
| 2001/0021872 A1 | 9/2001 | Bailey et al. |
| 2002/0026094 A1 | 2/2002 | Roth |
| 2002/0032481 A1 | 3/2002 | Gabbay |
| 2002/0138135 A1 | 9/2002 | Duerig et al. |
| 2002/0173842 A1 | 11/2002 | Buchanan |
| 2003/0004537 A1 | 1/2003 | Boyle et al. |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0039436 A1 | 2/2004 | Spenser et al. |
| 2004/0073165 A1 | 4/2004 | Musbach et al. |
| 2004/0098081 A1 | 5/2004 | Landreville et al. |
| 2004/0102791 A1 * | 5/2004 | Murray, III ............ A61F 2/958 606/108 |
| 2004/0133263 A1 | 7/2004 | Dusbabek et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0075728 A1 | 4/2005 | Nguyen et al. |
| 2005/0080474 A1 | 4/2005 | Andreas et al. |
| 2005/0096736 A1 | 5/2005 | Osse et al. |
| 2005/0188525 A1 | 9/2005 | Weber et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2005/0245894 A1 | 11/2005 | Zadno-Azizi |
| 2005/0288766 A1 | 12/2005 | Plain et al. |
| 2006/0004469 A1 | 1/2006 | Sokel |
| 2006/0025857 A1 | 2/2006 | Bergheim et al. |
| 2006/0058872 A1 | 3/2006 | Salahieh et al. |
| 2006/0149350 A1 | 7/2006 | Patel et al. |
| 2006/0183383 A1 | 8/2006 | Asmus et al. |
| 2006/0229719 A1 | 10/2006 | Marquez et al. |
| 2006/0259137 A1 | 11/2006 | Artof et al. |
| 2006/0282150 A1 | 12/2006 | Olson et al. |
| 2007/0005131 A1 | 1/2007 | Taylor |
| 2007/0005231 A1 | 1/2007 | Seguchi |
| 2007/0010876 A1 | 1/2007 | Salahieh et al. |
| 2007/0010877 A1 | 1/2007 | Salahieh et al. |
| 2007/0027534 A1 | 2/2007 | Bergheim et al. |
| 2007/0088431 A1 | 4/2007 | Bourang et al. |
| 2007/0112422 A1 | 5/2007 | Dehdashtian |
| 2007/0162102 A1 | 7/2007 | Ryan et al. |
| 2007/0203503 A1 | 8/2007 | Salahieh et al. |
| 2007/0203575 A1 | 8/2007 | Forster et al. |
| 2007/0203576 A1 | 8/2007 | Lee et al. |
| 2007/0213663 A1 | 9/2007 | Wang |
| 2007/0213813 A1 | 9/2007 | Von Segesser et al. |
| 2007/0233228 A1 | 10/2007 | Eberhardt et al. |
| 2007/0239254 A1 | 10/2007 | Chia et al. |
| 2007/0260305 A1 | 11/2007 | Drews et al. |
| 2007/0265700 A1 | 11/2007 | Eliasen et al. |
| 2007/0270943 A1 | 11/2007 | Solem et al. |
| 2007/0270944 A1 | 11/2007 | Bergheim et al. |
| 2008/0004571 A1 | 1/2008 | Voss |
| 2008/0065011 A1 | 3/2008 | Marchand et al. |
| 2008/0114442 A1 | 5/2008 | Mitchell et al. |
| 2008/0119922 A1 | 5/2008 | Alkhatib |
| 2008/0125853 A1 | 5/2008 | Bailey et al. |
| 2008/0154355 A1 | 6/2008 | Benichou et al. |
| 2008/0161911 A1 | 7/2008 | Revuelta et al. |
| 2008/0183271 A1 | 7/2008 | Frawley et al. |
| 2008/0275537 A1 | 11/2008 | Limon |
| 2008/0294230 A1 | 11/2008 | Parker |
| 2009/0124428 A1 | 5/2009 | Sullivan et al. |
| 2009/0125118 A1 | 5/2009 | Gong |
| 2009/0138079 A1 | 5/2009 | Tuval et al. |

(56) References Cited

U.S. PATENT DOCUMENTS

| | | |
|---|---|---|
| 2009/0157175 A1 | 6/2009 | Benichou |
| 2009/0164005 A1 | 6/2009 | Dove et al. |
| 2009/0171456 A1 | 7/2009 | Kveen et al. |
| 2009/0192585 A1 | 7/2009 | Bloom et al. |
| 2009/0234428 A1 | 9/2009 | Snow et al. |
| 2009/0254177 A1 | 10/2009 | Yang et al. |
| 2009/0276040 A1 | 11/2009 | Rowe et al. |
| 2009/0281619 A1 | 11/2009 | Le et al. |
| 2009/0299452 A1 | 12/2009 | Eidenschink et al. |
| 2009/0299456 A1 | 12/2009 | Melsheimer |
| 2009/0319037 A1 | 12/2009 | Rowe et al. |
| 2010/0030318 A1 | 2/2010 | Berra |
| 2010/0036472 A1 | 2/2010 | Papp |
| 2010/0036473 A1 | 2/2010 | Roth |
| 2010/0049313 A1 | 2/2010 | Alon et al. |
| 2010/0076402 A1 | 3/2010 | Mazzone et al. |
| 2010/0076541 A1 | 3/2010 | Kumoyama |
| 2010/0082089 A1 | 4/2010 | Quadri et al. |
| 2010/0094394 A1 | 4/2010 | Beach et al. |
| 2010/0121425 A1 | 5/2010 | Shimada |
| 2010/0145431 A1 | 6/2010 | Wu et al. |
| 2010/0168844 A1 | 7/2010 | Toomes et al. |
| 2010/0174363 A1 | 7/2010 | Castro |
| 2010/0198160 A1 | 8/2010 | Voss |
| 2010/0198347 A1 | 8/2010 | Zakay et al. |
| 2010/0204781 A1 | 8/2010 | Alkhatib |
| 2010/0274344 A1 | 10/2010 | Dusbabek et al. |
| 2011/0015729 A1 | 1/2011 | Jimenez et al. |
| 2011/0054596 A1 | 3/2011 | Taylor |
| 2011/0077731 A1* | 3/2011 | Lee ............ A61F 2/958 623/1.11 |
| 2011/0125132 A1 | 5/2011 | Krolik et al. |
| 2011/0144742 A1 | 6/2011 | Madrid et al. |
| 2011/0160846 A1 | 6/2011 | Bishop et al. |
| 2011/0166547 A1 | 7/2011 | Baumbach et al. |
| 2011/0190865 A1 | 8/2011 | McHugo et al. |
| 2011/0190867 A1 | 8/2011 | Vonderwalde et al. |
| 2011/0319991 A1 | 12/2011 | Hariton et al. |
| 2012/0083809 A1 | 4/2012 | Drasler et al. |
| 2012/0123529 A1 | 5/2012 | Levi et al. |
| 2012/0259409 A1 | 10/2012 | Nguyen et al. |
| 2013/0023985 A1 | 1/2013 | Khairkhahan et al. |
| 2013/0073035 A1 | 3/2013 | Tuval et al. |
| 2013/0190857 A1 | 7/2013 | Mitra et al. |
| 2013/0218266 A1 | 8/2013 | Chalekian et al. |
| 2013/0274873 A1 | 10/2013 | Delaloye et al. |
| 2013/0289607 A1 | 10/2013 | Pedersen et al. |
| 2013/0310926 A1 | 11/2013 | Hariton |
| 2013/0317598 A1 | 11/2013 | Rowe et al. |
| 2013/0331929 A1 | 12/2013 | Mitra et al. |
| 2014/0194981 A1 | 7/2014 | Menk et al. |
| 2014/0200661 A1 | 7/2014 | Pintor et al. |
| 2014/0209238 A1 | 7/2014 | Bonyuet et al. |
| 2014/0277417 A1 | 9/2014 | Schraut et al. |
| 2014/0277419 A1 | 9/2014 | Garde et al. |
| 2014/0277424 A1 | 9/2014 | Oslund |
| 2014/0330372 A1 | 11/2014 | Weston et al. |
| 2014/0343671 A1 | 11/2014 | Yohanan et al. |
| 2014/0350667 A1 | 11/2014 | Braido et al. |
| 2015/0073545 A1 | 3/2015 | Braido |
| 2015/0073546 A1 | 3/2015 | Braido |
| 2018/0036124 A1 | 2/2018 | Tran et al. |
| 2019/0125532 A1 | 5/2019 | Lee et al. |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 A1 | 3/1984 |
| EP | 0144167 A2 | 6/1985 |
| EP | 0597967 A1 | 5/1994 |
| EP | 0592410 B1 | 10/1995 |
| EP | 0850607 A1 | 7/1998 |
| EP | 1057460 A1 | 12/2000 |
| EP | 1088529 A2 | 4/2001 |
| EP | 1570809 A1 | 9/2005 |
| EP | 1796597 A2 | 6/2007 |
| FR | 2788217 A1 | 7/2000 |
| FR | 2815844 A1 | 5/2002 |
| GB | 2056023 A | 3/1981 |
| JP | 2002102354 A | 4/2002 |
| JP | 2002513298 A | 5/2002 |
| JP | 2002520121 A | 7/2002 |
| SU | 1271508 A1 | 11/1986 |
| WO | 9117720 A1 | 11/1991 |
| WO | 9217118 A1 | 10/1992 |
| WO | 9301768 A1 | 2/1993 |
| WO | 9724080 A1 | 7/1997 |
| WO | 9829057 A1 | 7/1998 |
| WO | 9930646 A1 | 6/1999 |
| WO | 9933414 A1 | 7/1999 |
| WO | 9940964 A1 | 8/1999 |
| WO | 9947075 A1 | 9/1999 |
| WO | 0018333 A1 | 4/2000 |
| WO | 0041652 A1 | 7/2000 |
| WO | 0047139 A1 | 8/2000 |
| WO | 0135878 A2 | 5/2001 |
| WO | 0149213 A2 | 7/2001 |
| WO | 0154624 A1 | 8/2001 |
| WO | 0154625 A1 | 8/2001 |
| WO | 0162189 A1 | 8/2001 |
| WO | 0164137 A1 | 9/2001 |
| WO | 0176510 A2 | 10/2001 |
| WO | 0195833 A2 | 12/2001 |
| WO | 0222054 A1 | 3/2002 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 0249540 A2 | 6/2002 |
| WO | 03047468 A1 | 6/2003 |
| WO | 2004037333 A1 | 5/2004 |
| WO | 2005013853 A2 | 2/2005 |
| WO | 2005034812 A1 | 4/2005 |
| WO | 2005084595 A1 | 9/2005 |
| WO | 2005087140 A1 | 9/2005 |
| WO | 2006014233 A2 | 2/2006 |
| WO | 2006032051 A2 | 3/2006 |
| WO | 2006034008 A2 | 3/2006 |
| WO | 06/108090 | 10/2006 |
| WO | 2006111391 A1 | 10/2006 |
| WO | 2006127089 A1 | 11/2006 |
| WO | 2006138173 A2 | 12/2006 |
| WO | 2005102015 A3 | 4/2007 |
| WO | 2007047488 A2 | 4/2007 |
| WO | 2007067942 A1 | 6/2007 |
| WO | 2007097983 A2 | 8/2007 |
| WO | 2008005405 A2 | 1/2008 |
| WO | 2008015257 A2 | 2/2008 |
| WO | 2008035337 A2 | 3/2008 |
| WO | 2008091515 A2 | 7/2008 |
| WO | 2008147964 A1 | 12/2008 |
| WO | 2008150529 A1 | 12/2008 |
| WO | 2009033469 A1 | 3/2009 |
| WO | 09/116041 | 9/2009 |
| WO | 2010121076 A2 | 10/2010 |
| WO | 2011146124 A1 | 11/2011 |

OTHER PUBLICATIONS

M.D. Dake, et al., "Transluminal Placement of Endovascular Stent-Grafts for the Treatment of Descending Thoracic Aortic Aneurysms," The New England Journal of Medicine. vol. 331, No. 26. 1994. pp. 1729-1734.

Andersen et al., "Transluminal Implantation of Artificial Heart Valves. Description of a New Expandable Aortic Valve and Initial

(56) References Cited

OTHER PUBLICATIONS

Results with Implantation by Catheter Technique in Closed Chest Pigs" European Heart Journal, 1992, 13, 704-708.
Andersen, H.R. "History of Percutaneous Aortic Valve Prosthesis," Herz No. 34. pp. 343-346. 2009.
Almagor et al., "Balloon Expandable Stent Implantation in Stenotic Right Heart Valved Conduits", Journal of the American College of Cardiology, vol. 16, No. 6, pp. 1310-1314, Nov. 15, 1990.
Sabbah et al., "Mechanical Factors in the Degeneration of Porcine Bioprosthetic Valves: An Overview", Journal of Cardiac Surgery, vol. 4, No. 4, pp. 302-309, Dec. 1989.
Serruys et al., "Stenting of Coronary Arteries. Are we the Sorcerer's Apprentice?", European Heart Journal, 10, 774-782, pp. 37-45, 1989.
Kolata, Gina "Device that Opens Clogged Arteries Gets a Failing Grade in a New Study", The New York Times, http://www.nytimes.com/1991/01/03/health/device-that-opens-clogged-arteries-gets-a-faili..., pp. 1-2, wrriten Jan. 3, 199, web page access Jul. 29, 2009.
Urban, M.D., Philip, "Coronary Artery Stenting," Editions Medecine et Hygiene, Geneve, 1991, pp. 5-47.
Al-Khaja et al., "Eleven Years' Experience with Carpentier-Edwards Biological Valves in Relation to Survival and Complications", European Journal of Cardio-thoracic Surgery 3: pp. 305-311, 1989.
Wheatley, M.D., David J., "Valve Prostheses," Rob & Smith's Operative Surgery, Fourth Edition, pp. 415-424, Butterworths 1986.
Benchimol, Alberto, et al., "Simultaneous Left Ventricular Echocardiography and Aortic Blood Velocity During Rapid Right Ventricular Pacing in Man," The American Journal of the Medical Sciences, Jan.-Feb. 1977 vol. 273, No. 1, pp. 55-62.
Watt, A.H., et al. "Intravenous Adenosine in the Treatment of Supraventricular Tachycardia; a Dose-Ranging Study and Interaction with Dipyridamole," British Journal of Clinical Pharmacology (1986), 21, 227-230.
Uchida, Barry T., et al., "Modifications of Gianturco Expandable Wire Stents," AJR:150, May 1988, Dec. 3, 1987, pp. 1185-1187.
Selby, M.D., J. Bayne, "Experience with New Retrieval Forceps for Foreign Body Removal in the Vascular, Urinary, and Biliary Systems," Radiology 1990; 176:535-538.
Inoune, M.D., Kanji, et al., "Clinical Application of Transvenous Mitral Commissurotomy by a New Balloon Catheter," The Journal of Thoracic and Cardiovascular Surgery 87:394-402, 1984.
Al Zaibag, Muayed, et al., "Percutaneous Balloon Valvotomy in Tricuspid Stenosis," British Heart Journal, Jan. 1987, vol. 57. No. 1, pp. 51-53.
Lawrence, Jr., M.D., David D., "Percutaneous Endovascular Graft: Experimental Evaluation," Radiology 1897; 163: 357-360.
Dotter et al., "Transluminal Treatment of Arteriosclerotic Obstruction: Description of a New Technic and a Preliminary Report of Its Application", Circulation, vol. XXX, pp. 654-670, 1964.
Sigwart, Ulrich, "An Overview of Intravascular Stents: Old and New," Chapter 48, Textbook of Interventional Cardiology, 2nd Edition, W.B. Saunders Company, Philadelphia, PA, © 1994, 1990, pp. 803-815.
Rashkind, M.D., William J., "Historical Aspects of Interventional Cardiology: Past, Present, Future," Texas Heart Institute Journal, Interventional Cardiology, 1986, pp. 363-367.
Rosch, M.D., Josef, "The Birth, Early Years and Future of Interventional Radiology," J Vasc Interv Radiol 2003; 14:841-853.
Pavcnik, M.D., Ph.D., Dusan, et al. "Development and Initial Experimental Evaluation of a Prosthetic Aortic Valve for Transcatheter Placement," Cardiovascular Radiology 1992; 183:151-154.
Ross, F.R.C.S, D.N., "Aortic Valve Surgery," Guy's Hospital, London, pp. 192-197, 1967.
Rashkind, M.D., William J., "Creation of an Atrial Septal Defect Withoput Thoracotomy," the Journal of the American Medical Association, vol. 196, No. 11, Jun. 13, 1966, pp. 173-174.
Porstmann, W., et al., "Der Verschlu.beta. des Ductus Arteriosus Persistens ohne Thorakotomie," Thoraxchirurgie Vaskulare Chirurgie, Band 15, Heft 2, Stuttgart, im Apr. 1967, pp. 199-203.

\* cited by examiner

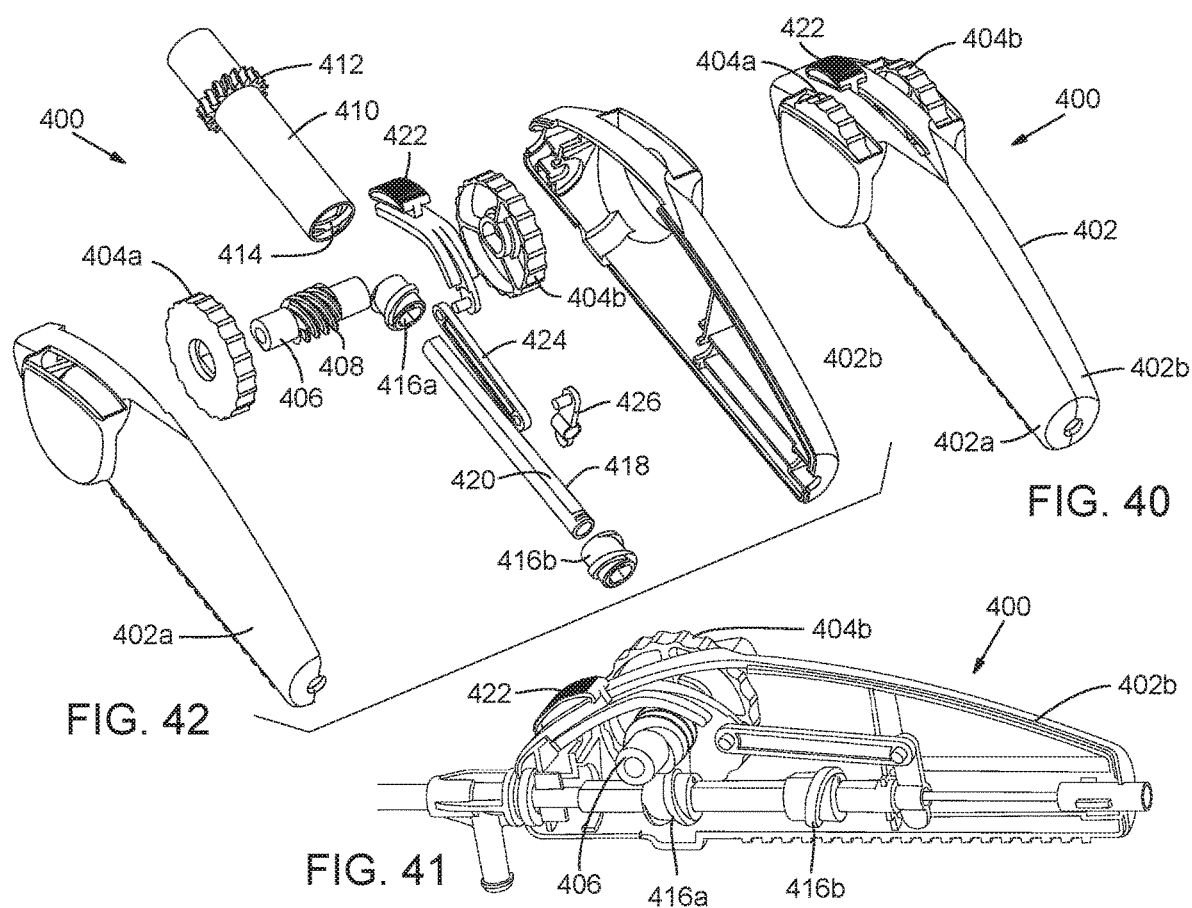

DELIVERY SYSTEMS FOR PROSTHETIC HEART VALVE

CROSS-REFERENCE TO RELATED APPLICATIONS

This application is a continuation of U.S. patent application Ser. No. 14/827,172, filed Aug. 14, 2015, which is a divisional of U.S. patent application Ser. No. 13/559,395, filed Jul. 26, 2012, now U.S. Pat. No. 9,119,716, issued Sep. 1, 2015, which claims the benefit of U.S. Provisional Patent Application No. 61/512,328, filed Jul. 27, 2011, all of which are incorporated by reference herein in their entirety.

FIELD

The present disclosure concerns embodiments of delivery systems for implanting prosthetic heart valves.

BACKGROUND

Prosthetic cardiac valves have been used for many years to treat cardiac valvular disorders. The native heart valves (such as the aortic, pulmonary and mitral valves) serve critical functions in assuring the forward flow of an adequate supply of blood through the cardiovascular system. These heart valves can be rendered less effective by congenital, inflammatory or infectious conditions. Such damage to the valves can result in serious cardiovascular compromise or death. For many years the definitive treatment for such disorders was the surgical repair or replacement of the valve during open heart surgery, but such surgeries are prone to many complications. More recently a transvascular technique has been developed for introducing and implanting a prosthetic heart valve using a flexible catheter in a manner that is less invasive than open heart surgery.

In this technique, a prosthetic valve is mounted in a crimped state on the end portion of a flexible catheter and advanced through a blood vessel of the patient until the prosthetic valve reaches the implantation site. The prosthetic valve at the catheter tip is then expanded to its functional size at the site of the defective native valve such as by inflating a balloon on which the prosthetic valve is mounted. Alternatively, the prosthetic valve can have a resilient, self-expanding stent or frame that expands the prosthetic valve to its functional size when it is advanced from a delivery sheath at the distal end of the catheter.

A prosthetic valve that has a relatively large profile or diameter in the compressed state can inhibit the physician's ability to advance the prosthetic valve through the femoral artery or vein. More particularly, a smaller profile allows for treatment of a wider population of patients, with enhanced safety. Thus, a need exists for delivery devices that can minimize the overall crimp profile of the prosthetic valve for the delivery of the prosthetic valve through the patient's vasculature.

Relatively long delivery devices, such as used for transfemoral delivery of a prosthetic valve, can inhibit the physician's ability to position the prosthetic valve precisely at the desired implantation site because the forces applied to the handle at one end of the delivery device can cause unwanted movement of the prosthetic valve at the opposite end of the delivery device. Thus, a need exists for delivery devices that allow a physician to accurately control the positioning of the prosthetic valve at the desired implantation location.

When introducing a delivery device into the body, an introducer sheath typically is inserted first and then the delivery device is inserted through the introducer sheath and into the body. If the prosthetic valve is mounted on a balloon catheter, the prosthetic valve can contact the inner surface of the introducer sheath and may become dislodged from its preferred location on the balloon catheter, depending on the size of the crimped valve. Thus, a need exists for delivery devices that can better retain the crimped valve at its desired location on the balloon catheter as it is advanced through an introducer sheath.

SUMMARY

Described herein are systems and methods for delivering prosthetic devices, such as prosthetic heart valves, through the body and into the heart for implantation therein. The prosthetic devices delivered with the delivery systems disclosed herein are, for example, radially expandable from a radially compressed state mounted on the delivery system to a radially expanded state for implantation using an inflatable balloon (or equivalent expansion device) of the delivery system. Exemplary delivery routes through the body and into the heart include transfemoral routes, transapical routes, and transaortic routes, among others. Although the devices and methods disclosed herein are particular suited for implanting prosthetic heart valves (e.g., a prosthetic aortic valve or prosthetic mitral valve), the disclosed devices and methods can be adapted for implanting other types of prosthetic valves within the body (e.g., prosthetic venous valves) or other types of expandable prosthetic devices adapted to be implanted in various body lumens.

In some embodiments, a delivery apparatus for implanting a prosthetic, transcatheter heart valve via a patient's vasculature includes an adjustment device for adjusting the position of a balloon relative to a crimped prosthetic valve (and/or vice versa). A balloon catheter can extend coaxially with a guide (or flex) catheter, and a balloon member at the distal end of the balloon catheter can be positioned proximal or distal to a crimped prosthetic valve. The balloon member and the crimped prosthetic valve can enter the vasculature of a patient through an introducer sheath and, once the balloon member and the crimped prosthetic valve reach a suitable location in the body, the relative position of the prosthetic valve and balloon member can be adjusted so that the balloon member is positioned within the frame of the prosthetic valve so that the prosthetic valve eventually can be expanded at the treatment site. Once the crimped prosthetic valve is positioned on the balloon, the prosthetic valve is advanced to the vicinity of the deployment location (i.e., the native aortic valve) and the adjustment device can further be used to accurately adjust or "fine tune" the position of the prosthetic valve relative to the desired deployment location.

An exemplary method of implanting a radially compressible and expandable prosthetic device (e.g., a prosthetic heart valve) in the heart comprises: (a) introducing a delivery device into the body of a patient, the delivery device comprising a handle portion, an elongated shaft extending from the handle portion, the shaft having a distal end portion mounting an inflatable balloon and a prosthetic heart valve in a radially compressed state; (b) advancing the distal end portion of the delivery device toward the native heart valve until the prosthetic valve is within or adjacent the annulus of the native heart valve; (c) positioning the prosthetic heart valve at a desired implantation position within the annulus of the native by rotating an adjustment device coupled to the handle portion and the shaft to cause the shaft and the prosthetic valve to move distally and/or proximally relative to the handle portion until the prosthetic heart valve is at the desired implantation position; and (d) after the prosthetic heart valve has been moved to the desired implantation position, inflating the balloon to cause the prosthetic heart valve to radially expand and engage the annulus of the native heart valve.

An exemplary delivery apparatus for implantation of a prosthetic device (e.g., a prosthetic heart valve) in the heart comprises an elongated shaft comprising a proximal end portion and a distal end portion, an inflatable balloon, and a valve mounting member. The balloon is mounted on the distal end portion of the shaft. The valve mounting member is disposed on the distal end portion of the shaft within the balloon and is configured to facilitate frictional engagement between the prosthetic heart valve and the balloon when the prosthetic heart valve is mounted in a radially compressed state on the balloon and surrounding the mounting member. The mounting member comprises at least one longitudinally extending fluid passageway though which an inflation fluid in the balloon can flow.

In some embodiments, the at least one fluid passageway has first and second openings adjacent first and second ends of the prosthetic heart valve, respectively. When the prosthetic valve is mounted on the balloon in a crimped state, the inflation fluid in the balloon can flow from a first region of the balloon proximal to the first end of the prosthetic valve, inwardly through the first opening, through the fluid passageway, outwardly through the second opening and into a second region of the balloon distal to the second end of the prosthetic valve.

Another exemplary delivery apparatus for implantation of a prosthetic device (e.g., a prosthetic heart valve) in the heart comprises a handle portion and an elongated shaft extending from the handle portion. The shaft comprises a proximal end portion coupled to the handle portion and a distal end portion configured to mount a prosthetic heart valve in a radially compressed state. The apparatus also comprises a sliding member disposed on the proximal end portion of the shaft. The handle portion comprising a rotatable member that is operatively coupled to the sliding member so as to cause translational movement of the sliding member upon rotation of the rotatable member. A shaft engagement member is disposed on the shaft and couples the shaft to the sliding member. The shaft engagement member is configured to be manipulated between a first state and a second state. In the first state, the shaft can move freely in the longitudinal direction relative to the sliding member and the rotatable member. In the second state, the shaft engagement member frictionally engages the shaft and prevents rotational and longitudinal movement of the shaft relative to the sliding member such that rotation of the rotatable member causes corresponding longitudinal movement of the sliding member and the shaft. When a prosthetic device is mounted on the distal end of the shaft and the shaft engagement member is manipulated to engage the shaft, the rotatable member can be used to adjust the location of the prosthetic device relative to its desired implantation location within the heart.

In some embodiments, the shaft engagement member comprises a collet disposed on the shaft. The collet can have flexible fingers that can be forced to frictionally engage and retain the shaft relative to the sliding member so that the rotatable member can be used to adjust the position of the prosthetic device mounted on the distal end portion of the shaft.

Another exemplary delivery device for implantation of a prosthetic device (e.g., a prosthetic heart valve) within the heart, such as via a transapical or transaortic route, comprises an inflatable balloon, a proximal stop, and a distal stop. The stops are configured to limit longitudinal movement of the prosthetic device relative to the balloon while the prosthetic device is mounted over the balloon in the radially compressed state between the proximal stop and the distal stop. The proximal stop and the distal stop each comprise an end portion positioned within the balloon and configured to be positioned adjacent the prosthetic device when the prosthetic device is radially compressed between the proximal and distal stops. Each of the stop end portions comprises at least one longitudinally extending slot that allows the respective stop end portion to be radially compressed to a smaller diameter. The at least one longitudinally extending slot in each stop end portion can also be configured to allow a balloon-inflation fluid to flow radially through the respective stop and into the region of the balloon extending through the prosthetic valve.

In some embodiments, when a prosthetic device is mounted on the delivery device in the radially compressed state, the proximal stop and the distal stop are configured to allow a balloon-inflation fluid to flow from a proximal portion of the balloon, through the at least one slot in the proximal stop, through an intermediate portion of the balloon positioned within the prosthetic device, through the at least one slot in the distal stop, and into a distal portion of the balloon.

In some embodiments, a proximal end of the balloon is attached to the proximal stop and a distal end of the balloon is attached to the distal stop.

In some embodiments, the delivery device further comprises an outer shaft having a lumen and an inner shaft extending through the lumen of the outer shaft, with the proximal stop attached to a distal end of the outer shaft and positioned around the inner shaft and the distal stop attached to an outer surface of the inner shaft.

In some embodiments, the proximal stop further comprises a proximal portion attached to the distal end of the outer shaft and to a proximal end of the balloon, and an intermediate portion extending between the proximal portion and the end portion, the intermediate portion having an outer diameter that is less than an outer diameter of the proximal portion and less than the diameter of the end portion.

In some embodiments, the proximal stop is attached to the distal end of the outer shaft and further comprises at least one fluid passageway that allows an inflation fluid to flow through the at least one passageway and into the balloon.

In some embodiments, the distal stop further comprises a distal portion attached to a distal end of the balloon and an intermediate portion extending between the distal portion and the end portion, the intermediate portion having an outer diameter that is less than an outer diameter of the distal portion and less than the diameter of the end portion.

In some embodiments, the end portion of each stop decreases in diameter in a direction extending away from the prosthetic device.

In some embodiments, the delivery device further comprises a nosecone attached to a distal end of the distal stop.

In some embodiments, at least one of the stop end portions comprises at least three longitudinal slots that allow the stop end portion to be radially compressed to a smaller diameter when the prosthetic device is crimped onto the delivery device.

An exemplary method of implanting a prosthetic heart valve within the heart comprises: (a) introducing a distal end portion of a delivery device into the native aortic valve of the heart, a distal end portion of the delivery device comprising an inflatable balloon, a proximal stop and a distal stop positioned at least partially within the balloon, and a radially expandable prosthetic heart valve mounted over the balloon and between the proximal stop and the distal stop in a radially compressed state; (b) inflating the balloon to radially expand the prosthetic heart valve within the native aortic valve, wherein the balloon is inflated with an inflation fluid that flows radially through the proximal and distal stops; (c) deflating the balloon; and (d) retracting the delivery device from the heart.

In some embodiments, the proximal stop is positioned adjacent to a proximal end of the prosthetic heart valve and the distal stop is positioned adjacent to a distal end of the prosthetic heart valve, such that the prosthetic device is longitudinally contained between the proximal and distal stops during introduction of the prosthetic heart valve through an introducer sheath into the body.

In some embodiments, inflating the balloon comprises causing the inflation fluid to flow: (i) through a first passageway in the proximal stop and into a proximal portion of the balloon; (ii) from the proximal portion of the balloon, through a second passageway in the proximal stop, and into an intermediate portion of the balloon within the prosthetic device; and (iii) from the intermediate portion of the balloon, through a passageway in the distal stop, and into a distal portion of the balloon.

In some embodiments, prior to introducing the delivery device into the heart, the prosthetic heart valve is crimped to the radially compressed state onto delivery device while the proximal stop and the distal stop are simultaneously radially compressed. The prosthetic heart valve can have a first outer diameter in the radially compressed state and the proximal stop and distal stop can be compressed from a second outer diameter to about the first outer diameter during the crimping. When compressive pressure is released after the crimping, the proximal stop and distal stop can be configured to resiliently expand from about the first outer diameter to about the second outer diameter.

An exemplary system for delivering a prosthetic device into a patient comprises an introducer sheath configured to be inserted partially into a patient, a loader configured to be inserted into a proximal end the introducer sheath, and a delivery device configured to be passed through the loader and the introducer sheath into the patient carrying a prosthetic device to be implanted in the patient. The loader comprises a flush port for selectively introducing fluid into the loader and a bleed port for selectively releasing fluid from within the loader, and both the flush port and the bleed port are sealed with the same resiliently flexible annular sealing member. The sealing member can comprise a push tab that extends radially through the bleed port, such that the bleed port is configured to be selectively opened by depressing the push tab in the radially inward direction.

The foregoing and other objects, features, and advantages of the invention will become more apparent from the following detailed description, which proceeds with reference to the accompanying figures.

BRIEF DESCRIPTION OF THE DRAWINGS

FIG. 40 is a perspective view of another embodiment of a handle that can be used in the delivery apparatus of FIG. 32.

FIG. 41 is a perspective of the handle of FIG. 40, with a portion of the outer housing and some internal components removed for purposes of illustration.

FIG. 42 is an exploded, perspective view of the handle of FIG. 40.

DETAILED DESCRIPTION

In particular embodiments, a delivery apparatus for implanting a prosthetic, transcatheter heart valve via a patient's vasculature includes an adjustment device for adjusting the position of a balloon relative to a crimped prosthetic valve (and/or vice versa). A balloon catheter can extend coaxially with a guide (or flex) catheter, and a balloon member at the distal end of the balloon catheter can be positioned proximal or distal to a crimped prosthetic valve. As described below in more detail, the balloon member and the crimped prosthetic valve can enter the vasculature of a patient through an introducer sheath and, once the balloon member and the crimped prosthetic valve reach a suitable location in the body, the relative position of the prosthetic valve and balloon member can be adjusted so that the balloon member is positioned within the frame of the prosthetic valve so that the prosthetic valve eventually can be expanded at the treatment site. Once the crimped prosthetic valve is positioned on the balloon, the prosthetic valve is advanced to the vicinity of the deployment location (i.e., the native aortic valve) and the adjustment device can further be used to accurately adjust or "fine tune" the position of the prosthetic valve relative to the desired deployment location.

Figure 1:
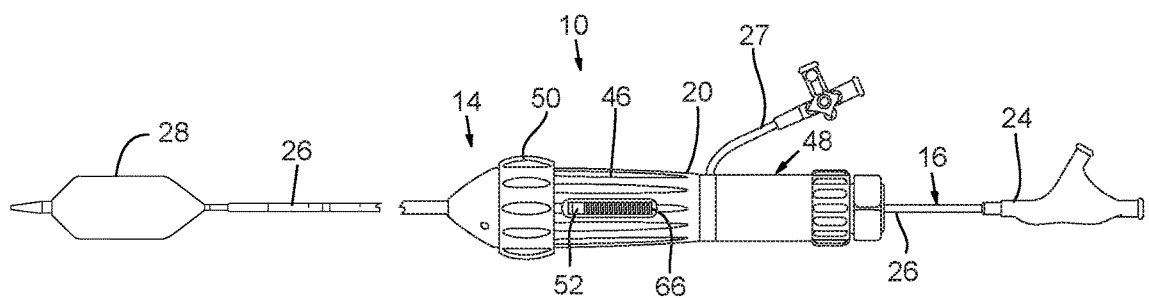
FIG. 1 is a side view of a delivery apparatus for implanting a prosthetic heart valve, according to one embodiment.

FIG. 1 shows a delivery apparatus 10 adapted to deliver a prosthetic heart valve 12 (shown schematically in FIGS. 9-11) (e.g., a prosthetic aortic valve) to a heart, according to one embodiment. The apparatus 10 generally includes a steerable guide catheter 14 (FIG. 3), and a balloon catheter 16 extending through the guide catheter 14. The guide catheter can also be referred to as a flex catheter or a main catheter. The use of the term main catheter should be understood, however, to include flex or guide catheters, as well as other catheters that do not have the ability to flex or guide through a patient's vasculature.

The guide catheter 14 and the balloon catheter 16 in the illustrated embodiment are adapted to slide longitudinally relative to each other to facilitate delivery and positioning of prosthetic valve 12 at an implantation site in a patient's body, as described in detail below.

Figure 3:
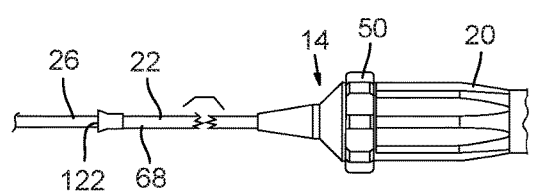
FIG. 3 is side view of a section of the handle and a section of the distal end portion of the delivery apparatus of FIG. 1.

The guide catheter 14 includes a handle portion 20 and an elongated guide tube, or shaft, 22 extending from handle portion 20 (FIG. 3). FIG. 1 shows the delivery apparatus without the guide catheter shaft 22 for purposes of illustration. FIG. 3 shows the guide catheter shaft 22 extending from the handle portion 20 over the balloon catheter. The balloon catheter 16 includes a proximal portion 24 (FIG. 1) adjacent handle portion 20 and an elongated shaft 26 that extends from the proximal portion 24 and through handle portion 20 and guide tube 22. The handle portion 20 can include a side arm 27 having an internal passage which fluidly communicates with a lumen defined by the handle portion 20.

Figure 4:
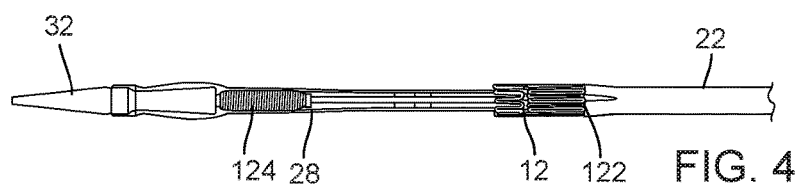
FIG. 4 is a side view of the distal end portion of the delivery apparatus of FIG. 1.

An inflatable balloon 28 is mounted at the distal end of balloon catheter 16. As shown in FIG. 4, the delivery apparatus 10 is configured to mount the prosthetic valve 12 in a crimped state proximal to the balloon 28 for insertion of the delivery apparatus and prosthetic valve into a patient's vasculature, which is described in detail in U.S. Publication No. 2009/0281619 (U.S. application Ser. No. 12/247,846, filed Oct. 8, 2008), which is incorporated herein by reference. Because prosthetic valve 12 is crimped at a location different from the location of balloon 28 (e.g., in this case prosthetic valve 12 desirably is crimped proximal to balloon 28), prosthetic valve 12 can be crimped to a lower profile than would be possible if prosthetic valve 12 was crimped on top of balloon 28. This lower profile permits the surgeon to more easily navigate the delivery apparatus (including crimped valve 12) through a patient's vasculature to the treatment location. The lower profile of the crimped prosthetic valve is particularly helpful when navigating through portions of the patient's vasculature which are particularly narrow, such as the iliac artery. The lower profile also allows for treatment of a wider population of patients, with enhanced safety.

A nose piece 32 (FIG. 4) can be mounted at the distal end of the delivery apparatus 10 to facilitate advancement of the delivery apparatus 10 through the patient's vasculature to the implantation site. In some instances, it may be useful to have nose piece 32 connected to a separate elongated shaft so that nose piece 32 can move independently of other elements of delivery apparatus 10. Nose piece 32 can be formed of a variety of materials, including various plastic materials.

Figure 5:
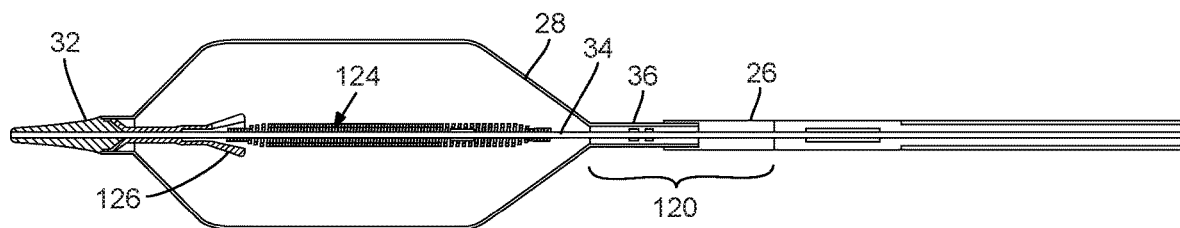
FIG. 5 is a side view of the distal end portion of the delivery apparatus of FIG. 1 showing the balloon in an inflated state.

As can be seen in FIG. 5, the balloon catheter 16 in the illustrated configuration further includes an inner shaft 34 (FIG. 2A) that extends from proximal portion 24 and coaxially through the outer balloon catheter shaft 26 and the balloon 28. The balloon 28 can be supported on a distal end portion of inner shaft 34 that extends outwardly from the outer shaft 26 with a proximal end portion 36 of the balloon secured to the distal end of outer shaft 26 (e.g., with a suitable adhesive) (FIG. 5). The outer diameter of inner shaft 34 is sized such that an annular space is defined between the inner and outer shafts along the entire length of the outer shaft. The proximal portion 24 of the balloon catheter can be formed with a fluid passageway (not shown) that is fluidly connectable to a fluid source (e.g., saline) for inflating the balloon. The fluid passageway is in fluid communication with the annular space between inner shaft 34 and outer shaft 26 such that fluid from the fluid source can flow through fluid passageway, through the space between the shafts, and into balloon 28 to inflate the same and deploy prosthetic valve 12.

The proximal portion 24 also defines an inner lumen that is in communication with a lumen 38 of the inner shaft 34 that is sized to receive guide wire (not shown) that can extend coaxially through the inner shaft 34 and the nose cone 32.

The inner shaft 34 and outer shaft 26 of the balloon catheter can be formed from any of various suitable materials, such as nylon, braided stainless steel wires, or a polyether block amide (commercially available as Pebax®). The shafts 26, 34 can have longitudinal sections formed from different materials in order to vary the flexibility of the shafts along their lengths. The inner shaft 34 can have an inner liner or layer formed of Teflon® to minimize sliding friction with a guide wire.

The distal end portion of the guide catheter shaft 22 comprises a steerable section 68 (FIG. 3), the curvature of which can be adjusted by the operator to assist in guiding the apparatus through the patient's vasculature, and in particular, the aortic arch. The handle 20 in the illustrated embodiment comprises a distal handle portion 46 and a proximal handle portion 48. The distal handle portion 46 functions as a mechanism for adjusting the curvature of the distal end portion of the guide catheter shaft 22 and as a flex indicating device that allows a user to measure the relative amount of flex of the distal end of the guide catheter shaft 22. In addition, the flex indicating device provides a visual and tactile response at the handle the device, which provides a surgeon with an immediate and direct way to determine the amount of flex of the distal end of the catheter.

Figure 2A:
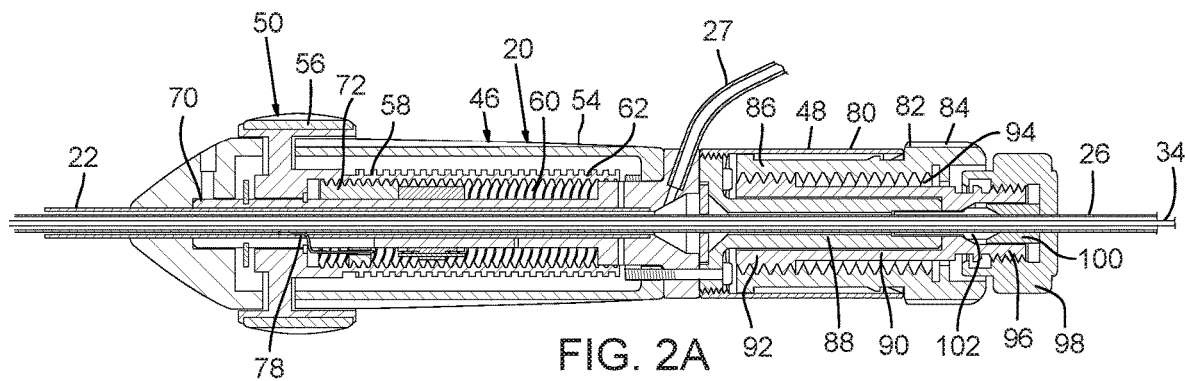
FIG. 2A is a cross-sectional view of the handle of the delivery apparatus of FIG. 1.
Figure 2B:
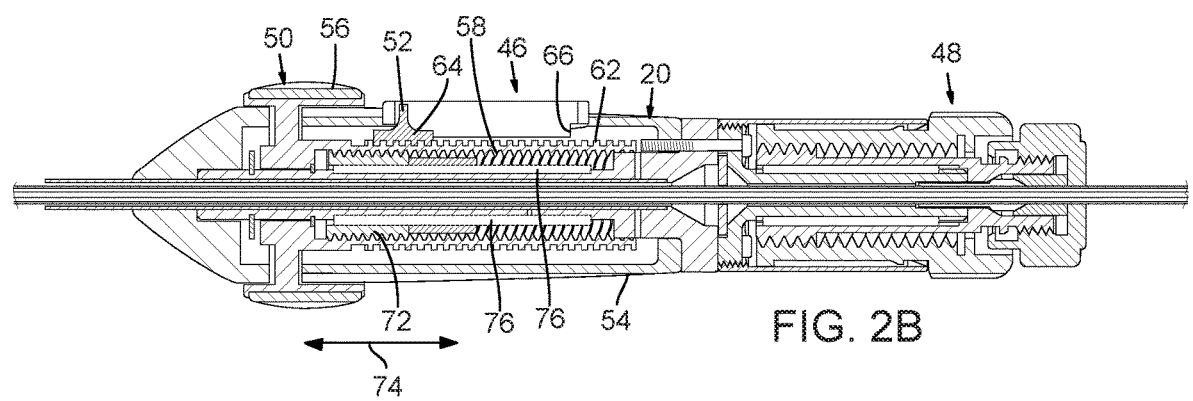
FIG. 2B is another cross-sectional view of the handle of the delivery apparatus of FIG. 1.

The distal handle portion 46 can be operatively connected to the steerable section 68 and functions as an adjustment mechanism to permit operator adjustment of the curvature of the steerable section via manual adjustment of the handle portion. Explaining further, the handle portion 46 comprises a flex activating member 50, an indicator pin 52, and a cylindrical main body, or housing 54. As shown in FIGS. 2A and 2B, the flex activating member 50 comprises an adjustment knob 56 and a shaft 58 extending proximally from the knob into the housing 54. A proximal end portion of the guide catheter shaft 22 extends into and is fixed within the central lumen of the housing 54. An inner sleeve 70 surrounds a portion of the guide catheter shaft 22 inside the housing 54. A threaded slide nut 72 is disposed on and is slidable relative to the sleeve 70. The slide nut 72 is formed with external threads that mate with internal threads 60 of the shaft 58.

The slide nut 72 can be formed with two slots formed on the inner surface of the nut and extending the length thereof. The sleeve 70 can be formed with longitudinally extending slots that are aligned with the slots of the slide nut 72 when the slide nut is placed on the sleeve. Disposed in each slot is a respective elongated nut guide, which can be in the form of an elongated rod or pin 76. The nut guides 76 extend radially into respective slots in the slide nut 72 to prevent rotation of the slide nut 72 relative to the sleeve 70. By virtue of this arrangement, rotation of the adjustment knob 56 (either clockwise or counterclockwise) causes the slide nut 72 to move longitudinally relative to the sleeve 70 in the directions indicated by double-headed arrow 74.

One or more pull wires 78 (FIG. 2A) couple the adjustment knob 56 to the steerable section 68 to adjust the curvature of the steerable section upon rotation of the adjustment knob. For example, the proximal end portion of the pull wire 78 can extend into and can be secured to a retaining pin, such as by crimping the pin around the proximal end of the pull wire, which pin is disposed in a slot in the slide nut 72. The pull wire extends from the pin, through the slot in the slide nut, a slot in the sleeve 70, and into and through a pull wire lumen in the shaft 22. The distal end portion of the pull wire is secured to the distal end portion of the steerable section 68.

The pin, which retains the proximal end of the pull wire 78, is captured in the slot in the slide nut 72. Hence, when the adjustment knob 56 is rotated to move the slide nut 72 in the proximal direction, the pull wire also is moved in the proximal direction. The pull wire pulls the distal end of the steerable section 68 back toward the handle portion, thereby bending the steerable section and reducing its radius of curvature. The friction between the adjustment knob 56 and the slide nut 72 is sufficient to hold the pull wire taut, thus preserving the shape of the bend in the steerable section if the operator releases the adjustment knob 56. When the adjustment knob 56 is rotated in the opposite direction to move the slide nut 72 in the distal direction, tension in the pull wire is released. The resiliency of the steerable section 68 causes the steerable to return its normal, non-deflected shape as tension on the pull wire is decreased. Because the pull wire is not fixedly secured to the slide nut 72 (the pin can move within the slot in the nut), movement of the slide nut in the distal direction does not push on the end of the pull wire, causing it to buckle. Instead, the pin is allowed to float within the slot of the slide nut 72 when the knob 56 is adjusted to reduce tension in the pull wire, preventing buckling of the pull wire.

In particular embodiments, the steerable section 68 in its non-deflected shape is slightly curved and in its fully curved position, the steerable section generally conforms to the shape of the aortic arch. In other embodiments, the steerable section can be substantially straight in its non-deflected position.

The distal handle portion 46 can have other configurations that are adapted to adjust the curvature of the steerable section 68. One such alternative handle configuration is shown in co-pending U.S. patent application Ser. No. 11/152,288 (published under Publication No. US 2007/0005131), which is incorporated herein by reference in its entirety. Additional details relating to the steerable section and handle configuration discussed above can be found in U.S. patent application Ser. No. 11/852,977 (published as U.S. Publication No. US2008/0065011), which is incorporated herein by reference in its entirety.

The shaft 58 also includes an externally threaded surface portion 62. As shown in FIG. 2B, a base portion 64 of the indicator pin 52 mates with the externally threaded surface portion 62 of the shaft 58. The shaft 58 extends into the main body 54 and the indicator pin 52 is trapped between the externally threaded surface portion 62 and the main body 54, with a portion of the indicator pin 52 extending into a longitudinal slot 66 of the handle. As the knob 56 rotated to increase the curvature of the distal end of the guide catheter shaft 22, the indicator pin 52 tracks the external threaded portion 62 of the flex activating member and moves in the proximal direction inside of the slot 66. The greater the amount of rotation of the knob 56, the further indicator pin 52 moves towards the proximal end of the proximal handle portion 46. Conversely, rotating the knob 56 in the opposite direction decreases the curvature of the distal end of the guide catheter shaft 22 (i.e., straightens the guide catheter shaft) and causes corresponding movement of the indicator pin 52 toward the distal end of the distal handle portion 46.

The outer surface of the main body 54 of the distal handle portion 46 can include visual indicia adjacent the slot 66 that indicate the amount of flex of the distal end of the guide catheter shaft 22, based on the position of the indicator pin 52 relative to the visual indicia. Such indicia can identify the amount of flex in any of a variety of manners. For example, the outer surface of the main body 54 can include a series of numbers (e.g., 0 to 10) adjacent the slot that indicate the amount of curvature of the guide catheter shaft 22 based on the position of the indicator pin 52 relative to the number scale.

As described above, when the delivery apparatus is introduced into the vasculature of the patient, a crimped prosthetic valve 12 is positioned proximal to the balloon 28 (FIG. 4). Prior to expansion of the balloon 28 and deployment of prosthetic valve 12 at the treatment site, the prosthetic valve 12 is moved relative to the balloon (or vice versa) to position the crimped prosthetic valve on the balloon for deploying (expanding) the prosthetic valve. As discussed below, the proximal handle portion 48 serves as an adjustment device that can be used to move the balloon 28 proximally into position within the frame of prosthetic valve 12, and further to accurately position the balloon and the prosthetic valve at the desired deployment location.

As shown in FIGS. 2A and 2B, the proximal handle portion 48 comprises an outer housing 80 and an adjustment mechanism 82. The adjustment mechanism 82, which is configured to adjust the axial position of the balloon catheter shaft 26 relative to the guide catheter shaft 22, comprises an adjustment knob 84 and a shaft 86 extending distally into the housing 80. Mounted within the housing 80 on the balloon catheter shaft 26 is an inner support 88, which in turn mounts an inner shaft 90 (also referred to as a slider or sliding mechanism) (also shown in FIG. 22). The inner shaft 90 has a distal end portion 92 formed with external threads that mate with internal threads 94 that extend along the inner surface of the adjustment mechanism 82. The inner shaft 90 further includes a proximal end portion 96 that mounts a securement mechanism 98, which is configured to retain the position of the balloon catheter shaft 26 relative to the proximal handle portion 48 for use of the adjustment mechanism 82, as further described below. The inner shaft 90 can be coupled to the inner support 88 such that rotation of shaft 86 causes the inner shaft 90 to move axially within the handle. For example, the inner support 88 can have an axially extending rod or rail that extends into slot formed in the inner surface of the inner shaft 90. The rod or rail prevents rotation of the inner shaft 90 but allows it to move axially upon rotation of the shaft 86.

The securement mechanism 98 includes internal threads that mate with external threads of the proximal end portion 96 of the inner shaft. Mounted within the proximal end portion 96 on the balloon catheter shaft 26 is a pusher element 100 and a shaft engagement member in the form of a collet 102. The collet 102 is configured to be manipulated by the securement mechanism between a first state in which collet allows the balloon catheter shaft to be moved freely in the longitudinal and rotational directions and a second state in which the collet frictionally engages the balloon catheter shaft and prevents rotational and longitudinal movement of the balloon catheter shaft relative to the inner shaft 90, as further described below.

Figure 6:
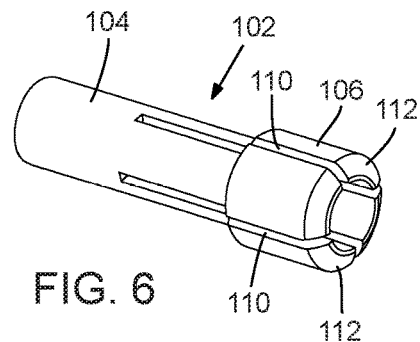
FIG. 6 is an enlarged perspective view of a collet used in the handle of the delivery apparatus of FIG. 1.
Figure 7:
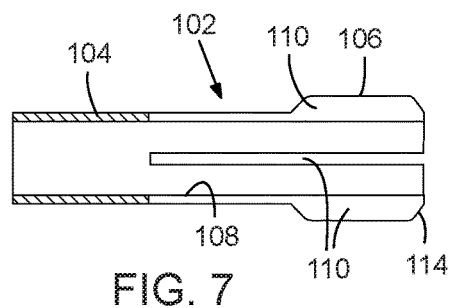
FIG. 7 is a cross-sectional view of the collet of FIG. 6.

As best shown in FIGS. 6 and 7, the collet 102 comprises a distal end portion 104, an enlarged proximal end portion 106, and a lumen 108 that receives the balloon catheter shaft 26. A plurality of axially extending, circumferentially spaced slots 110 extend from the proximal end of the collet to a location on the distal end portion 104, thereby forming a plurality of flexible fingers 112. The proximal end portion can be formed with a tapered end surface 114 that engages a corresponding tapered end surface of the pusher element 100 (FIG. 2A).

As noted above, the securement mechanism 98 is operable to restrain movement of the balloon catheter shaft 26 (in the axial and rotational directions) relative to the proximal handle portion 48. Explaining further, the securement mechanism 98 is movable between a proximal position (shown in FIGS. 2A and 2B) and a distal position closer to the adjacent end of the knob 84. In the proximal position, the collet 102 applies little, if any, force against the balloon catheter shaft 26, which can slide freely relative to the collet 102, the entire handle 20, and the guide catheter shaft 22. When the securement mechanism 98 is rotated so as to move to its distal position closer to knob 84, the securement mechanism urges pusher element 100 against the proximal end of the collet 102. The tapered surface of the pusher element pushes against the corresponding tapered surface 114 of the collet, forcing fingers 112 radially inward against the outer surface of the balloon catheter shaft 26. The holding force of the collet 102 against the balloon catheter shaft locks the balloon catheter shaft relative to the inner shaft 90. In the locked position, rotation of the adjustment knob 84 causes the inner shaft 90 and the balloon catheter shaft 26 to move axially relative to the guide catheter shaft 22 (either in the proximal or distal direction, depending on the direction the knob 84 is rotated).

The adjustment knob 84 can be utilized to position the prosthetic valve 12 on the balloon 28 and/or once the prosthetic valve 12 is on the balloon, to position the prosthetic valve and the balloon at the desired deployment site within the native valve annulus. One specific method for implanting the prosthetic valve 12 in the native aortic valve is as follows. The prosthetic valve 12 initially can be crimped on a mounting region 120 (FIGS. 4 and 5) of the balloon catheter shaft 26 immediately adjacent the proximal end of the balloon 28 or slightly overlapping the proximal end of the balloon. The proximal end of the prosthetic valve can abut the distal end 122 of the guide catheter shaft 22 (FIG. 4), which keeps the prosthetic valve in place on the balloon catheter shaft as the delivery apparatus and prosthetic valve are inserted through an introducer sheath. The prosthetic valve 12 can be delivered in a transfemoral procedure by first inserting an introducer sheath into the femoral artery and pushing the delivery apparatus through the introducer sheath into the patient's vasculature.

Figure 9:
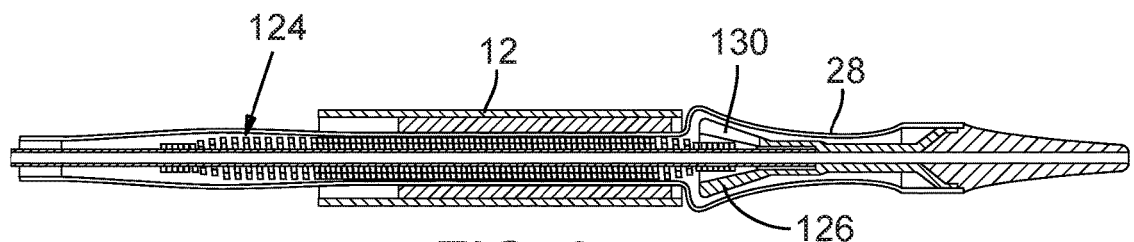
FIGS. 9-11 are enlarged, cross-sectional views of the distal end portion of the delivery apparatus of FIG. 1, showing the inflation of a balloon for deployment of a prosthetic heart valve on the balloon.

After the prosthetic valve 12 is advanced through the narrowest portions of the patient's vasculature (e.g., the iliac artery), the prosthetic valve 12 can be moved onto the balloon 28. For example, a convenient location for moving the prosthetic valve onto the balloon is the descending aorta. The prosthetic valve can be moved onto the balloon, for example, by holding the handle portion 46 steady (which retains the guide catheter shaft 22 in place), and moving the balloon catheter shaft 26 in the proximal direction relative to the guide catheter shaft 22. As the balloon catheter shaft is moved in the proximal direction, the distal end 122 of the guide catheter shaft pushes against the prosthetic valve, allowing the balloon 28 to be moved proximally through the prosthetic valve in order to center the prosthetic valve on the balloon, as depicted in FIG. 9. The balloon catheter shaft can include one or more radiopaque markers to assist the user in positioning the prosthetic valve at the desired location on the balloon. The balloon catheter shaft 26 can be moved in the proximal direction by simply sliding/pulling the balloon catheter shaft in the proximal direction if the securement mechanism 98 is not engaged to retain the shaft 26. For more precise control of the shaft 26, the securement mechanism 98 can be engaged to retain the shaft 26, in which case the adjustment knob 84 is rotated to effect movement of the shaft 26 and the balloon 28.

As shown in FIG. 5, the delivery apparatus can further include a mounting member 124 secured to the outer surface of the shaft 34 within the balloon 28. The mounting member helps retain the prosthetic valve in place on the balloon by facilitating the frictional engagement between the prosthetic valve and the outer surface of the balloon. The mounting member 124 helps retain the prosthetic valve in place for final positioning of the prosthetic valve at the deployment location, especially when crossing the native leaflets, which typically are calcified and provide resistance against movement of the prosthetic valve. The nose cone 32 can include a proximal portion 126 inside the balloon to assist in positioning the prosthetic valve. The proximal portion 126 desirably comprises a tapered member that has a maximum diameter at its proximal end adjacent the distal end of the prosthetic valve (FIG. 9) and tapers in a direction toward the distal end of the nosecone 32. The tapered member 126 serves as a transition section between the nosecone and the prosthetic valve as the prosthetic valve is pushed through the calcified native leaflets by shielding the distal end of the prosthetic valve from contacting the native leaflets. Although FIG. 9 shows the prosthetic valve having a crimped diameter slightly larger than the diameter of the tapered member 126 at its proximal end, the tapered member 126 can have a diameter at its proximal end that is the same as or slightly larger than the diameter of the crimped prosthetic valve, or at least the same as or slightly larger than the diameter of the metal frame of the crimped prosthetic valve.

As shown in FIG. 9, the prosthetic valve desirably is positioned on the balloon for deployment such that the distal end of the prosthetic valve is slightly spaced from the nose cone portion 126. When the prosthetic valve is positioned as shown in FIG. 9, the guide catheter shaft 22 can be moved proximally relative to the balloon catheter shaft 26 so that the guide catheter shaft is not covering the inflatable portion of the balloon 28, and therefore will not interfere with inflation of the balloon.

As the prosthetic valve 12 is guided through the aortic arch and into the ascending aorta, the curvature of the steerable section 68 can be adjusted (as explained in detail above) to help guide or steer the prosthetic valve through that portion of the vasculature. As the prosthetic valve is moved closer toward the deployment location within the aortic annulus, it becomes increasingly more difficult to control the precise location of the prosthetic valve by pushing or pulling the handle portion 20 due to the curved section of the delivery apparatus. When pushing or pulling the handle portion 20, slack is removed from the curved section of the delivery apparatus before the pushing/pulling force is transferred to the distal end of the delivery apparatus. Consequently, the prosthetic valve tends to "jump" or move abruptly, making precise positioning of the prosthetic valve difficult.

For more accurate positioning of the prosthetic valve within the aortic annulus, the prosthetic valve 12 is placed as close as possible to its final deployment location (e.g., within the aortic annulus such that an inflow end portion of the prosthetic valve is in the left ventricle and an outflow end portion of the prosthetic valve is in the aorta) by pushing/pulling the handle 20, and final positioning of the prosthetic valve is accomplished using the adjustment knob 84. To use the adjustment knob 84, the securement mechanism 98 is placed in its locked position, as described above. Then, the handle 20 is held steady (which retains the guide catheter shaft 22 in place) while rotating the adjustment knob 84 to move the balloon catheter shaft 26, and thus the prosthetic valve, in the distal or proximal directions. For example, rotating the knob in a first direction (e.g., clockwise), moves the prosthetic valve proximally into the aorta, while rotating the knob in a second, opposite direction (e.g., counterclockwise) advances the prosthetic valve distally toward the left ventricle. Advantageously, operation of the adjustment knob 84 is effective to move the prosthetic valve in a precise and controlled manner without sudden, abrupt movements as can happen when pushing or pulling the delivery apparatus for final positioning.

Figure 11:
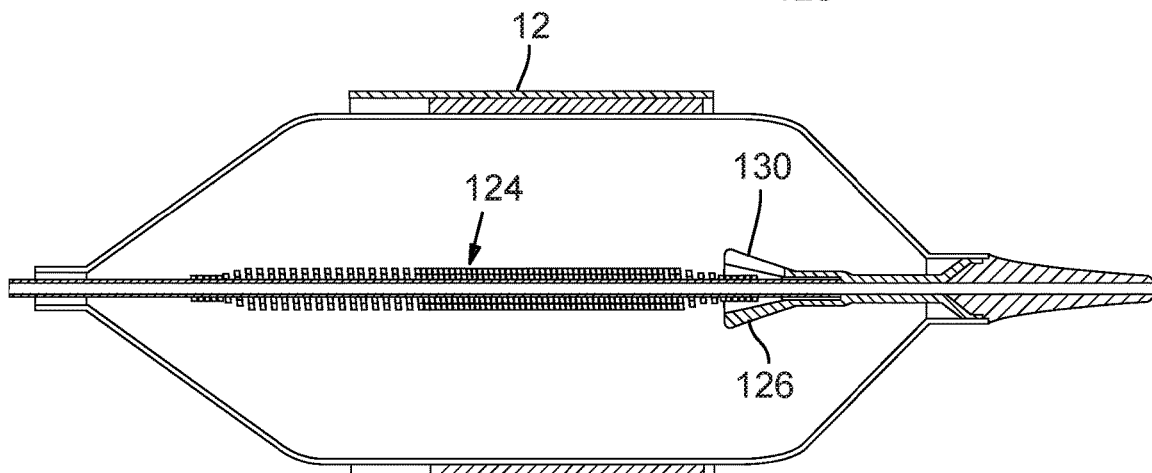

When the prosthetic valve is at the deployment location, the balloon 28 is inflated to expand the prosthetic valve 12 (as depicted in FIG. 11) so as to contact the native annulus. The expanded prosthetic valve becomes anchored within the native aortic annulus by the radial outward force of the valve's frame against the surrounding tissue.

Figure 8:
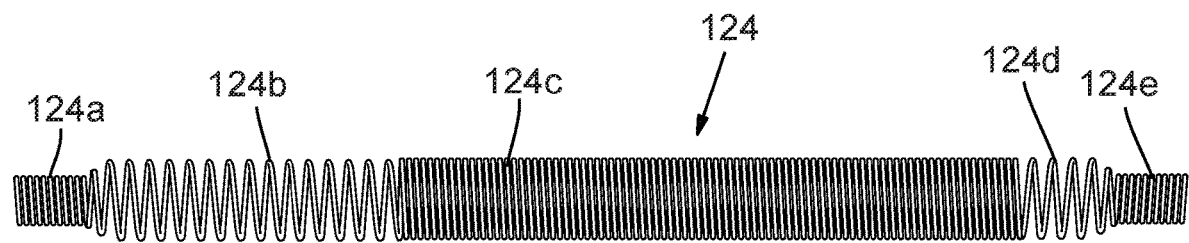
FIG. 8 is an enlarged side view of a mounting member for a prosthetic heart valve.

The mounting member 124 within the balloon is configured to allow the inflation fluid (e.g., saline) to flow unobstructed from the proximal end of the balloon to the distal end of the balloon. As best shown in FIG. 8, for example, the mounting member 124 comprises a coiled wire (e.g., a metal coil) having a first section 124a, a second section 124b, a third section 124c, a fourth section 124d, and a fifth section 124e. When the prosthetic valve 12 is positioned on the balloon for deployment, the second section 124b is immediately adjacent the proximal end of the prosthetic valve and the fourth section 124d is immediately adjacent the distal end of the prosthetic valve. The first and fifth sections 124a, 124e, respectively, which are at the proximal and distal ends of the mounting member, respectively, are secured to the balloon catheter shaft. The second, third, and fourth sections 124b, 124c, and 124d, respectively, are relatively larger in diameter than the first and fifth sections and are spaced radially from the outer surface of the balloon catheter shaft. As can be seen, the second section 124b and the fourth section 124d are formed with spaces between adjacent coils. The third section can be formed with smaller spaces (or no spaces) between adjacent coils to maximize the surface area available to retain the prosthetic valve on the balloon during final positioning of the prosthetic valve at the deployment location.

Figure 10:
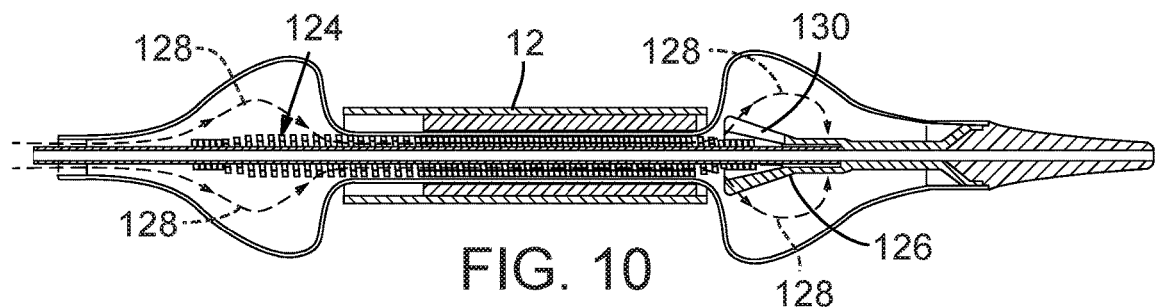

Referring to FIG. 10, the spacing between coils of the second and fourth sections 124b, 124d allows the inflation fluid to flow radially inwardly through the coils of the second section 124b, axially through the lumen of the third section 124c, radially outwardly through the coils of the fourth section 124d, into the distal section of the balloon, in the direction of arrows 128. The nose cone portion 126 also can be formed with one or more slots 130 that allow the inflation fluid to flow more easily past the proximal nose cone portion 126 into the distal section of the balloon. In the illustrated embodiment, the proximal nose cone portion 126 has three circumferentially spaced slots 130. Since the inflation fluid can pressurize and inflate the proximal and distal sections of the balloon at substantially the same rate, the balloon can be inflated more evenly for controlled, even expansion of the prosthetic valve.

Figure 12:
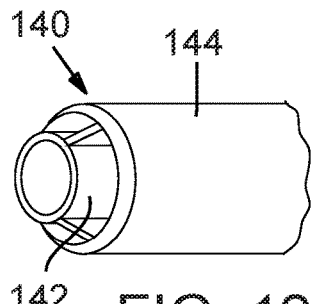
FIG. 12 is a perspective view of an alternative embodiment of a mounting member for a prosthetic heart valve.
Figure 13:
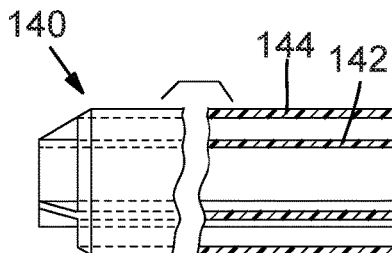
FIG. 13 is a side view of the mounting member of FIG. 12 shown partially in section.
Figure 14:
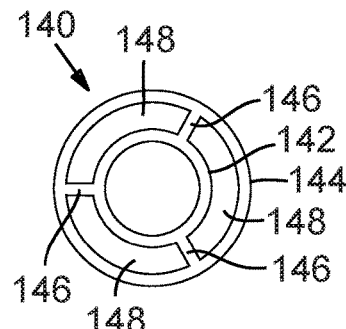
FIG. 14 is an end view of the mounting member of FIG. 12.
Figure 15:
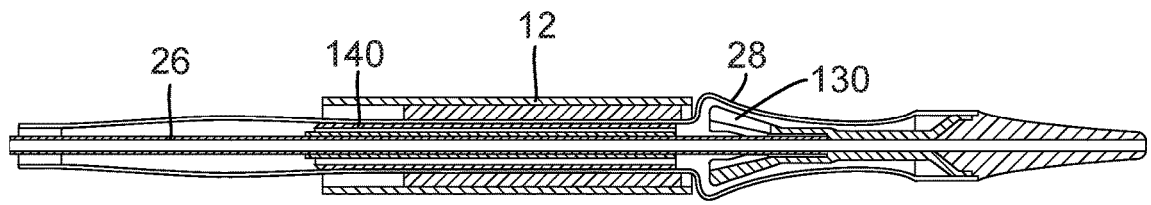
FIGS. 15-17 are enlarged, cross-sectional views of the distal end portion of a delivery apparatus containing the mounting member of FIG. 12, and showing the inflation of a balloon for deployment of a prosthetic heart valve on the balloon.
Figure 16:
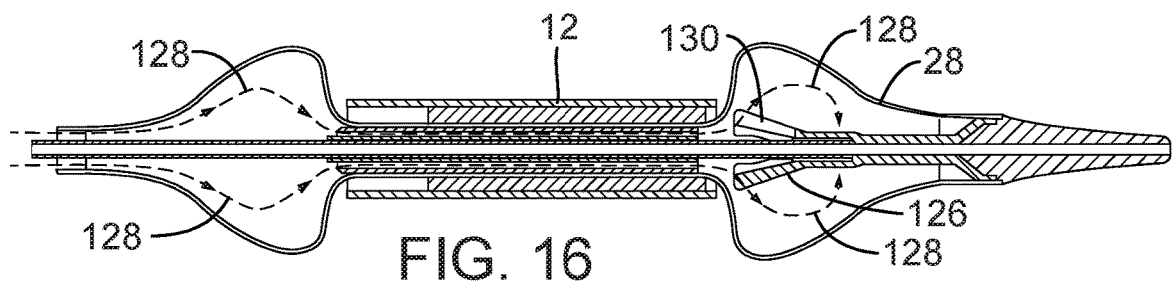
Figure 17:
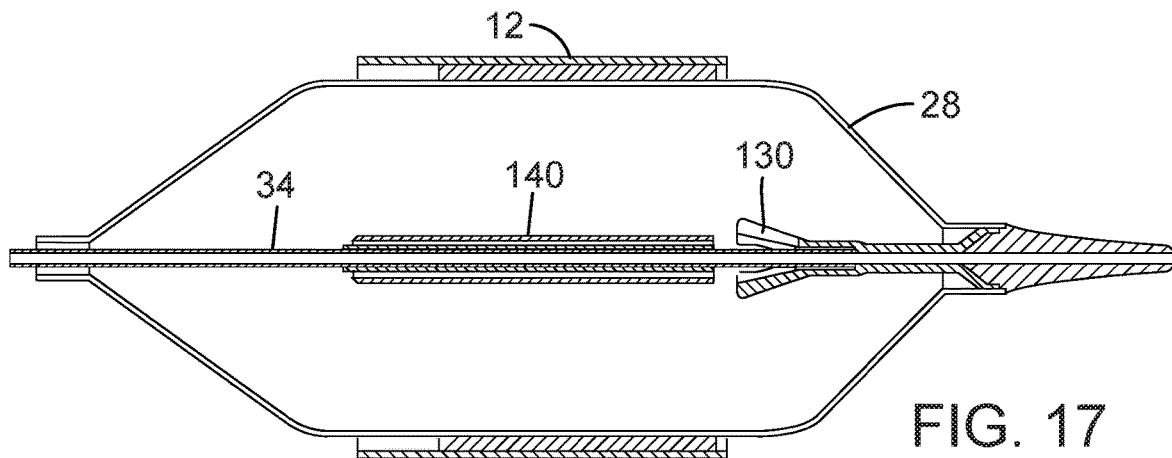

FIGS. 12-14 illustrate a mounting member 140 according to another embodiment. The mounting member 140 comprises a cylindrical inner wall 142, a cylindrical outer wall 144, and a plurality of angularly spaced ribs 146 separating the inner and outer walls. The inner wall 142 is secured to the outer surface of the shaft 34 within the balloon. In particular embodiments, the mounting member 140 can be made of a relatively rigid material (e.g., polyurethane or another suitable plastic) that does not radially compress when the prosthetic valve is moved onto the balloon. As shown in FIG. 16, during inflation of the balloon, inflation fluid in the proximal section of the balloon can flow through the spaces 148 between the inner and outer walls of the mounting member, through one or more slots 130 in the proximal nose cone portion 126, and into the distal section of the balloon, in the direction of arrows 128.

It should be noted that the location of the threaded portions of the adjustment mechanism 82 and the inner shaft 90 can be reversed. That is, adjustment mechanism 82 can have an externally threaded portion that engages an internally threaded portion of the inner shaft 90. In addition, for embodiments where the balloon 28 is initially positioned proximal to the prosthetic valve 12, the adjustment mechanism 82 can be used to move the balloon distally relative to the crimped prosthetic valve in order to center the prosthetic valve on the balloon for deployment.

Figure 56:
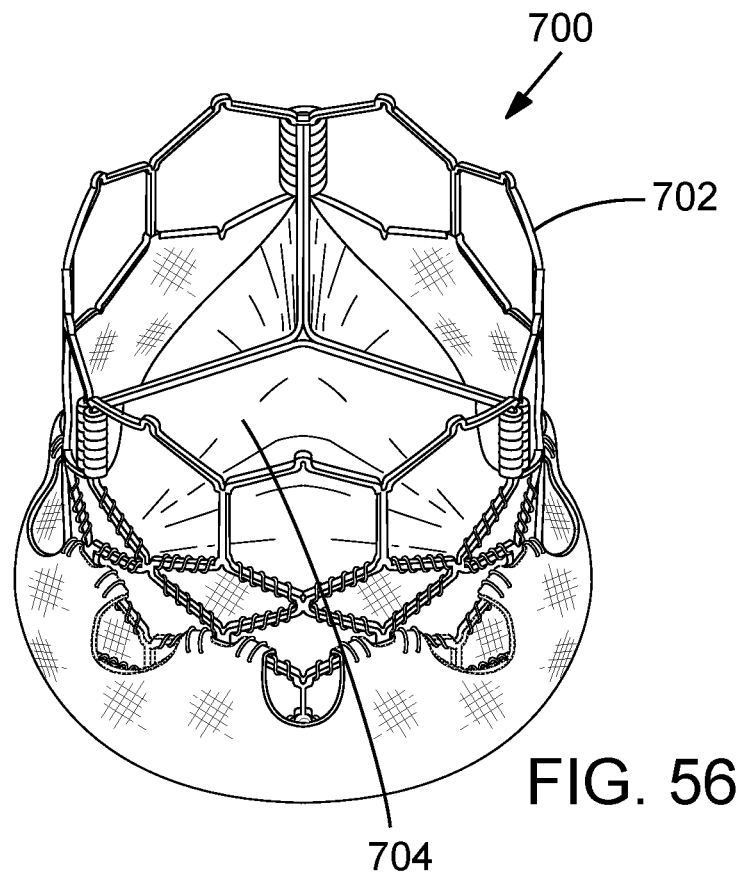
FIG. 56 is a perspective view of a prosthetic heart valve, according to one embodiment.
Figure 57:
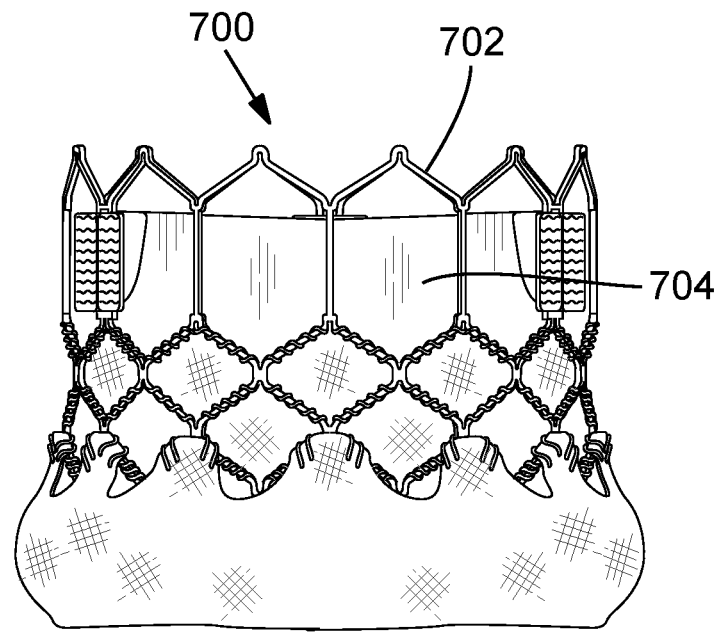
FIG. 57 is a side elevation view of the prosthetic heart valve of FIG. 56.

FIGS. 56 and 57 show a prosthetic heart valve 700, according to another embodiment. The heart valve 700 comprises a frame, or stent, 702 and a leaflet structure 704 supported by the frame. In particular embodiments, the heart valve 700 is adapted to be implanted in the native aortic valve and can be implanted in the body using, for example, the delivery apparatus 10 described above. The prosthetic valve 700 can also be implanted within the body using any of the other delivery apparatuses described herein. Thus, the frame 702 typically comprises a plastically expandable material, such as stainless steel, a nickel based alloy (e.g., a nickel-cobalt-chromium alloy), polymers, or combinations thereof. In other embodiments, the prosthetic valve 12, 700 can be a self-expandable prosthetic valve with a frame made from a self-expanding material, such as Nitinol. When the prosthetic valve is a self-expanding valve, the balloon of the delivery apparatus can be replaced with a sheath or similar restraining device that retains the prosthetic valve in a radially compressed state for delivery through the body. When the prosthetic valve is at the implantation location, the prosthetic valve can be released from the sheath, and therefore allowed to expand to its functional size. It should be noted that any of the delivery apparatuses disclosed herein can be adapted for use with a self-expanding valve.

Figures 18, 19:
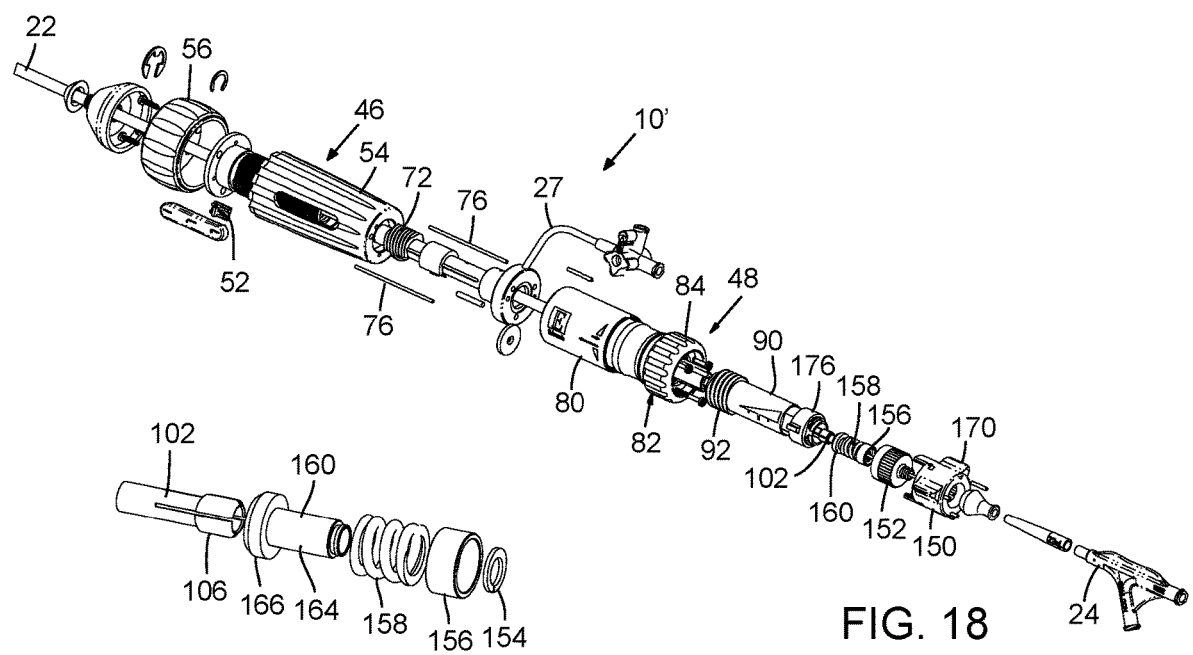
FIG. 18 is an exploded perspective view of the handle of a delivery apparatus, according to another embodiment.
FIG. 19 is an enlarged perspective view of the collet, pusher element, spring, ring, and washer of the handle shown in FIG. 18.

FIG. 18 is an exploded, perspective view of the distal end section of an alternative embodiment of a delivery device, indicated at 10'. The delivery device 10' shares many similarities with the delivery device 10, and therefore components of the delivery device 10' that are the same as those in the delivery device 10 are given the same reference numerals and are not described further. One difference between the delivery device 10 and the delivery device 10' is that the latter includes a different mechanism for locking/securing the balloon catheter shaft 26 relative to the adjustment knob 84.

Figure 20:
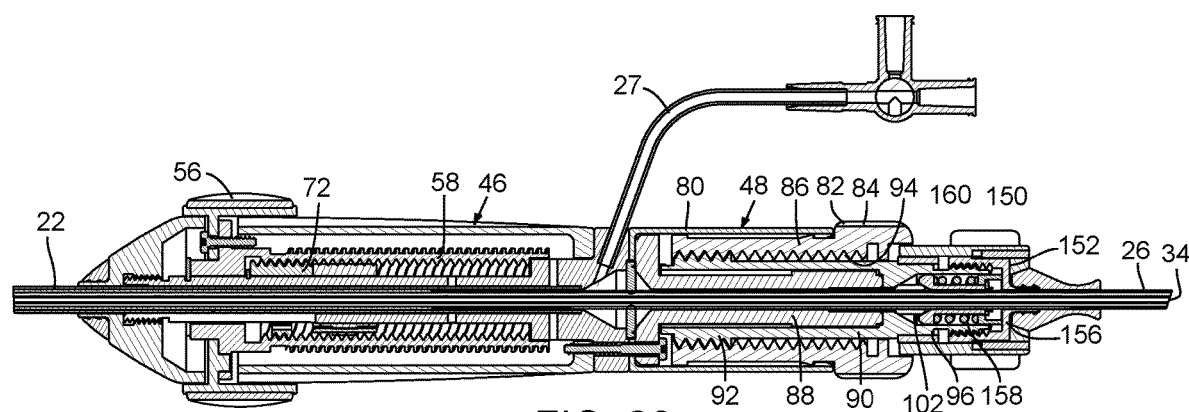
FIG. 20 is a cross-sectional view of the handle of the delivery apparatus of FIG. 18.
Figure 21:
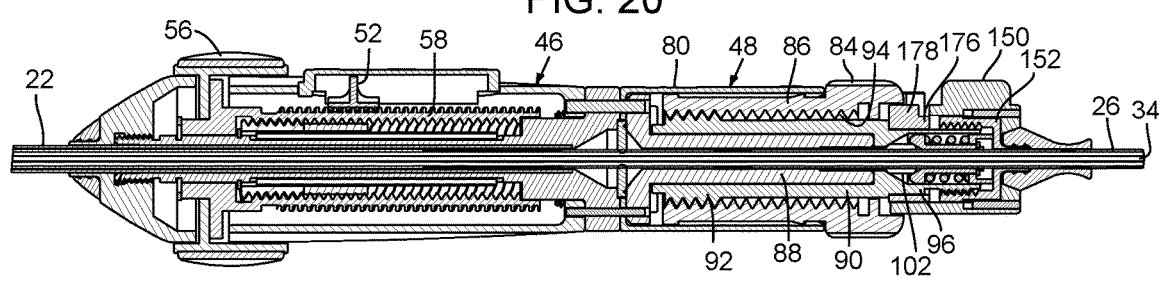
FIG. 21 is another cross-sectional view of the handle of the delivery apparatus of FIG. 18.
Figure 22:
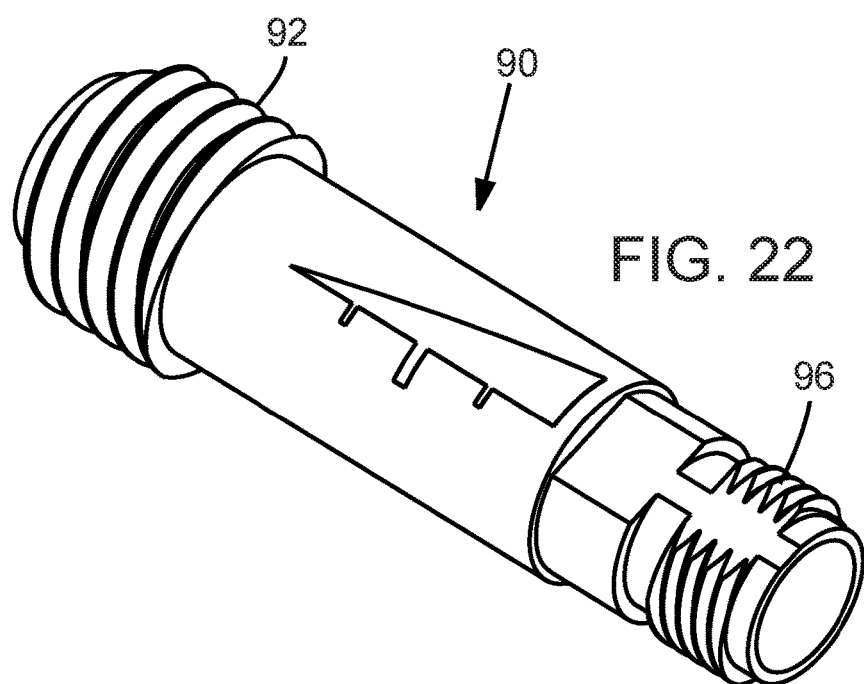
FIG. 22 is a perspective view of the inner shaft, or slider, of the handle shown in FIG. 18.
Figure 23:
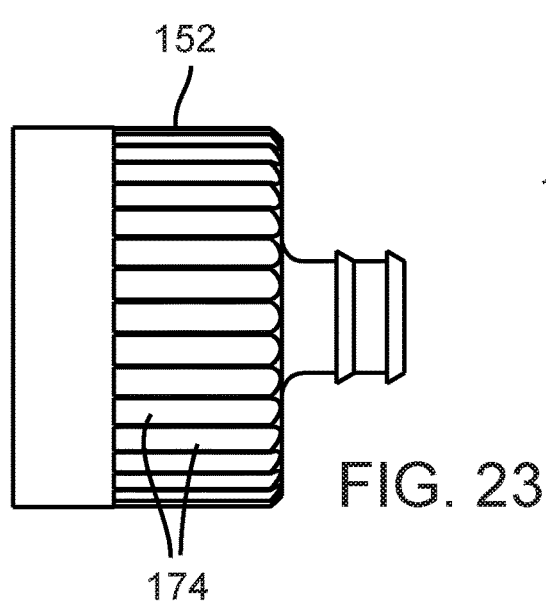
FIG. 23 is an enlarged side view of the inner nut of the handle shown in FIG. 18.
Figure 24:
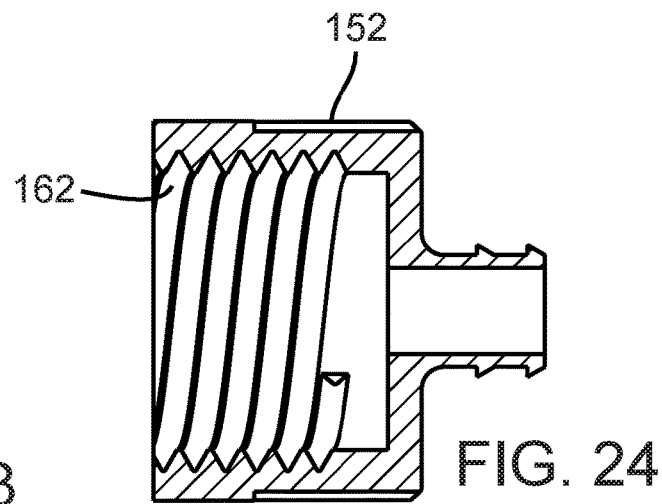
FIG. 24 is an enlarged cross-sectional view of the inner nut shown in FIG. 23.

Referring to FIGS. 18 and 19, the locking mechanism for the balloon catheter shaft comprises an adjustment knob 150 housing an inner nut 152, a washer 154 and a ring 156 disposed inside the inner nut 152, a biasing member in the form of a coiled spring 158, a pusher element 160, and a shaft engagement member in the form of a collet 102. As best shown in FIGS. 20 and 21, the inner nut 152 includes inner threads 162 (FIG. 24) that engage the external threads of the distal end portion 96 of the inner shaft 90 (FIG. 22). The pusher element 160 includes a proximal shaft 164 and an enlarged distal end portion 166 that bears against the proximal end portion 106 of the collet 102. The spring 158 is disposed on the shaft 164 of the pusher element 160 and has a proximal end that bears against the ring 156 and a distal end that bears against the distal end portion 166 of the pusher element 160.

Figure 25:
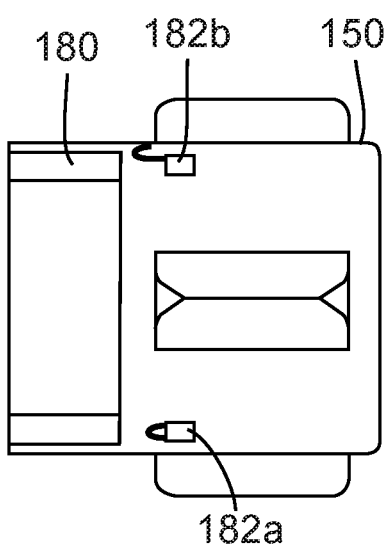
FIGS. 25-27 are enlarged top, perspective and end views, respectively, of the rotatable knob of the handle shown in FIG. 18.
Figure 26:
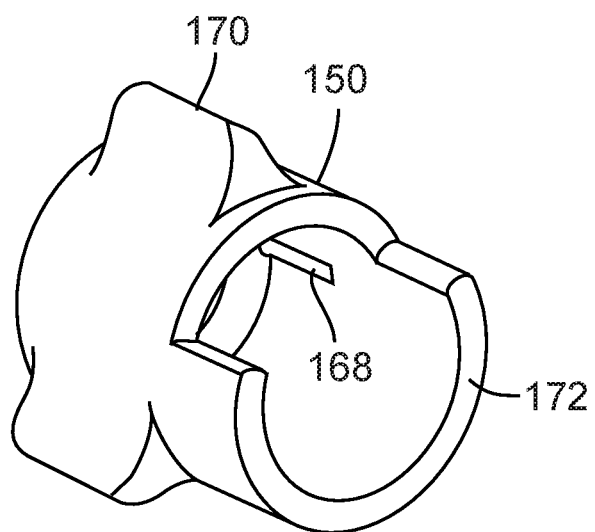
Figure 27:
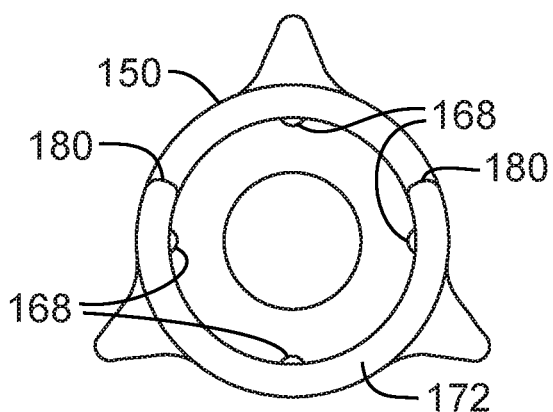
Figure 28:
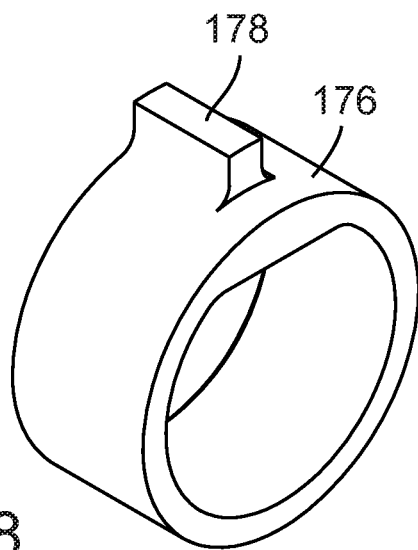
FIG. 28 is an enlarged perspective view of the indicator ring of the handle shown in FIG. 18.

Referring to FIGS. 25-27, the adjustment knob 150 is formed with a plurality of longitudinally extending, circumferentially spaced projections 168 on the inner surface of the knob. A distal portion of the knob 150 includes one or more radially extending projections 170 for gripping by a user and a proximal portion of the knob comprises a semi-annular portion 172. The knob 150 extends co-axially over the inner nut 152 with the projections 168 mating with respective grooves 174 on the outer surface of the nut 152 such that rotation of the knob causes corresponding rotation of the nut 152.

The delivery device 10' can be used in the manner described above in connection with the delivery device 10 to deliver a prosthetic valve in the vicinity of the implantation site. To restrain movement of the balloon catheter shaft 26 for fine positioning of the prosthetic valve, the knob 150 is rotated, which in turn causes rotation of the inner nut 152. The inner nut 152 is caused to translate in the distal direction along the external threads on the distal end portion 96 of the shaft 90. As the nut 152 is moved distally, the nut 152 pushes against the ring 156, which in turn pushes against the spring 158. The spring 158 presses against the distal end portion 166 of the pusher element 160, urging the pusher element against the collet 102. The pushing force of the pusher element 160 against the collet causes the fingers 112 of the collet to frictionally engage the balloon catheter shaft 26, thereby retaining the balloon catheter shaft relative to the inner shaft 90. In the locked position, rotation of the adjustment knob 84 causes the inner shaft 90 and the balloon catheter shaft 26 to move axially relative to the guide catheter shaft 22 (either in the proximal or distal direction, depending on the direction the knob 84 is rotated).

The biasing force of the spring 158 desirably is sufficient to lock the collet against the balloon catheter shaft with a relatively small degree of rotation of the knob 150, such as less than 360 degrees rotation of the knob. In the illustrated embodiment, the knob 150 is rotated less than 180 degrees from an unlocked position (in which the collet does not retain the balloon catheter shaft) to a locked position (in which the collet frictionally engages and retains the balloon catheter shaft). Conversely, rotating the knob 150 in the opposite direction from the locked position to the unlocked position through the same degree of rotation allows the spring 158 to release the biasing force against the pusher element and the collet so as to permit axial movement of the balloon catheter shaft relative to the collet.

As best shown in FIG. 21, an indicator ring 176 is disposed on the shaft 90 adjacent the proximal end of the knob 84. The indicator ring 176 sits within the semi-annular wall 172 of the knob 150 and includes an indicator tab 178 that extends into the annular space between the ends 180 (FIG. 27) of the semi-annular wall 172. As best shown in FIG. 25, the outer surface of the knob 150 can include visual indicia that indicate whether the balloon catheter shaft 26 is in a locked state relative to the adjustment knob 84. In the illustrated implementation, for example, a first indicia 182a is located adjacent one end 180 of the semi-annular wall 172 and a second indicia 182b is located adjacent the other end 180 of the semi-annular wall 172. The first indicia 182a is a graphical representation of a closed lock (indicating that the balloon catheter shaft is in a locked state) and the second indicia 182b is a graphical representation of an open lock (indicating that the balloon catheter shaft is in an unlocked state). However, it should be understood that the indicia can take various other forms (text and/or graphics) to indicate the locked and unlocked states.

Since the indicator ring 176 is fixed rotationally relative to the knob 150, the indicator tab 178 limits rotation of the knob 150 through an arc length defined by the annular space between the ends 180 of the semi-annular wall 172 (about 170 degrees in the illustrated embodiment). When the knob 150 is rotated in a first direction (counterclockwise in the illustrated example), the indicator tab 178 will contact the wall end 180 adjacent indicia 182b and prevent further rotation of the knob 150. In this position, the collet 102 does not frictionally engage the balloon catheter shaft 26, which can be moved freely relative to the proximal handle portion 48. When the knob 150 is rotated in a second direction (clockwise in the illustrated example), the indicator tab 178 will contact the wall end 180 adjacent indicia 182a and prevent further rotation of the knob 150. In this position, the collet 102 is caused to frictionally engage the balloon catheter shaft in the manner described above to restrain axial and rotational movement of the balloon catheter shaft relative to the proximal handle portion 48.

Figure 29:
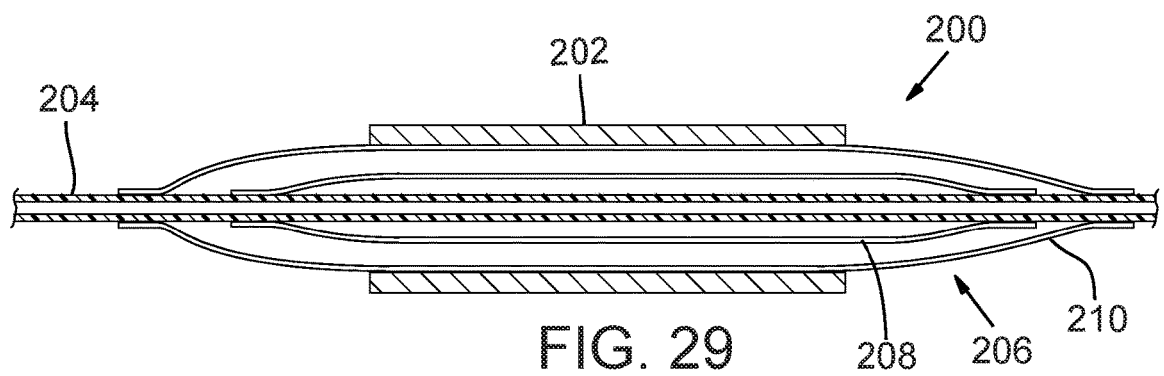
FIGS. 29-31 are cross-sectional views of the distal end portion of a delivery apparatus for a prosthetic heart valve, according to another embodiment, having two inflatable balloons for deploying a prosthetic valve.
Figure 30:
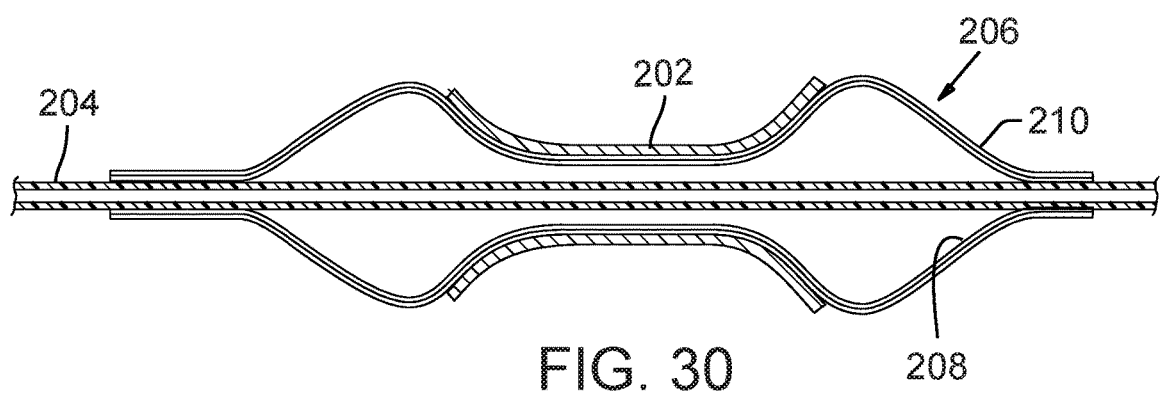
Figure 31:
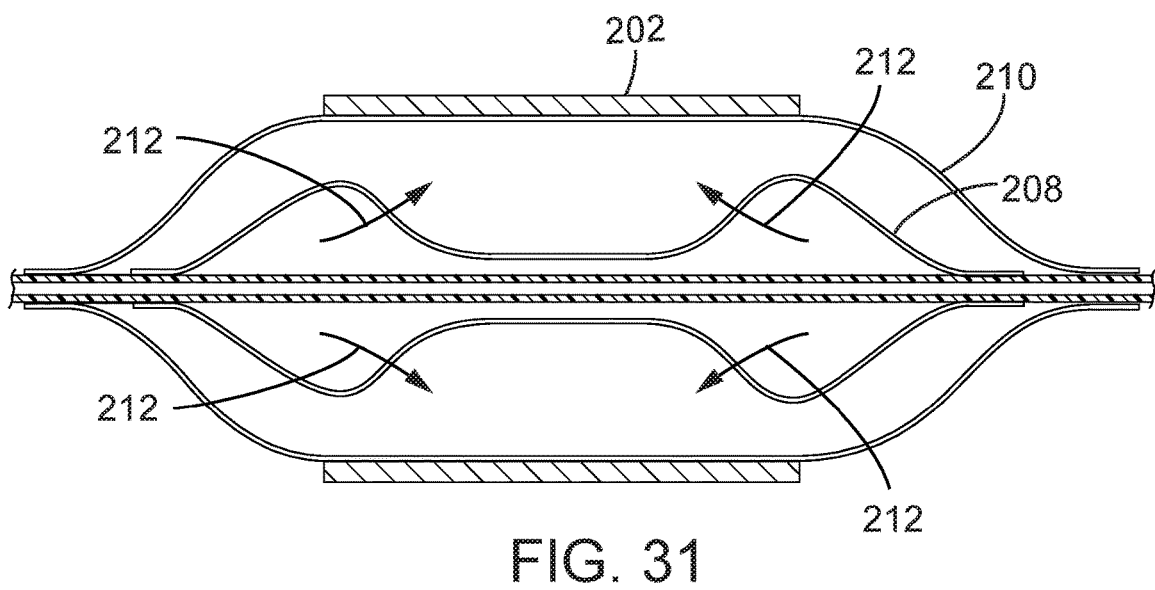

FIGS. 29-31 show the distal end portion of a balloon catheter 200, according to another embodiment, that can be used to implant an intraluminal implant, such as a stent or a stented prosthetic valve. The features of the balloon catheter 200 can be implemented in the delivery apparatuses disclosed herein (e.g., apparatus 10 of FIG. 1). In the figures, a prosthetic valve is shown schematically and is identified by reference numeral 202. The balloon catheter 200 includes a balloon catheter shaft 204. The proximal end of the shaft 204 is mounted to a handle (not shown) and the distal end of the shaft mounts a balloon assembly 206.

The balloon assembly 206 comprises an inner balloon 208 disposed inside an outer balloon 210. The inner balloon 208 is shaped to control expansion of the prosthetic valve 202 while the outer balloon is shaped to define the final expanded shape of the prosthetic valve. For example, as shown in FIG. 30, the inner balloon 208 can have a "dog bone" shape when inflated, having bulbous end portions that taper inwardly to form a generally cylindrical center portion of a reduced diameter. The shape of the inner balloon 208 helps maintain the position of the prosthetic valve relative to the balloon as the prosthetic valve is expanded due to the larger end portions that restrict movement of the prosthetic valve in the axial directions. The distal end portion of the shaft 204 can have openings to allow an inflation fluid to flow from the lumen of the shaft 204 into the inner balloon 208.

The inner balloon 208 can be formed with small pores or openings that are sized to permit suitable inflation of the inner balloon and allow the inflation fluid to flow outwardly into the space between the two balloons to inflate the outer balloon, as indicated by arrows 212. After the inner balloon is inflated, which partially expands the prosthetic valve 202 (FIG. 30), the inflation fluid begins inflating the outer balloon 210 (FIG. 31). Inflation of the outer balloon further expands the prosthetic valve 202 to its final desired shape (e.g., cylindrical as shown in FIG. 31) against the surrounding tissue. In such a two-stage expansion of the prosthetic valve 202, the position of the prosthetic valve relative to the shaft 204 can be controlled due to the inner balloon, which limits axial movement of the prosthetic valve during its initial expansion.

In an alternative embodiment, in lieu of or in addition to the pores or holes in the inner balloon, the inner balloon can be configured to burst at a predetermined pressure (e.g., 1-5 bars) after it is inflated to a desired size. After the inner balloon ruptures, the inflation fluid can begin inflating the outer balloon.

Figure 32:
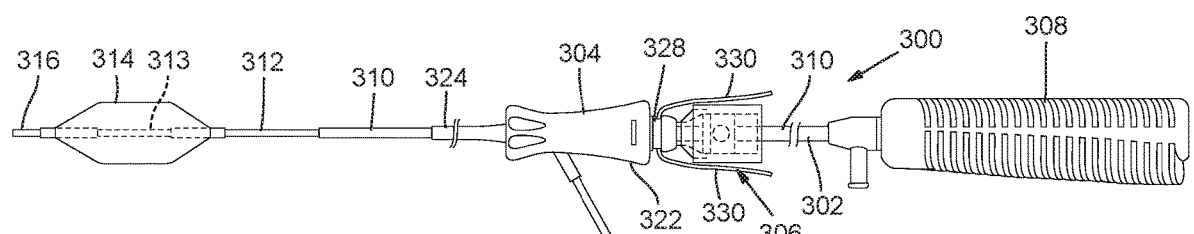
FIG. 32 is a side view of a delivery apparatus for a prosthetic heart valve, an introducer, and a loader device, according to another embodiment.

FIG. 32 discloses a delivery system 300, according to another embodiment, that can be used to implant an expandable prosthetic valve. The delivery system 300 is specifically adapted for use in introducing a prosthetic valve into a heart in a transapical procedure, which is disclosed in co-pending application Ser. No. 12/835,555, filed Jul. 13, 2010 (U.S. Publication No. 2011/0015729), which is incorporated herein by reference. In a transapical procedure, a prosthetic valve is introduced into the left ventricle through a surgical opening in the apex of the heart. The delivery system 300 similarly can be used for introducing a prosthetic valve into a heart in a transaortic procedure. In a transaortic procedure, a prosthetic valve is introduced into the aorta through a surgical incision in the ascending aorta, such as through a partial J-sternotomy or right parasternal mini-thoracotomy, and then advanced through the ascending aorta toward heart.

The delivery system comprises a balloon catheter 302, an introducer 304, and a loader 306. The balloon catheter 302 comprises a handle 308, an outer flush shaft 310 extending from the handle, an articulating main shaft 312 extending from the handle 308 coaxially through the outer shaft 310, an inner shaft 313 extending from the handle coaxially through the articulating shaft 312, an inflatable balloon 314 mounted on the shaft 312, and a nose cone 316 mounted on the inner shaft 313 distal to the balloon.

Figure 33:
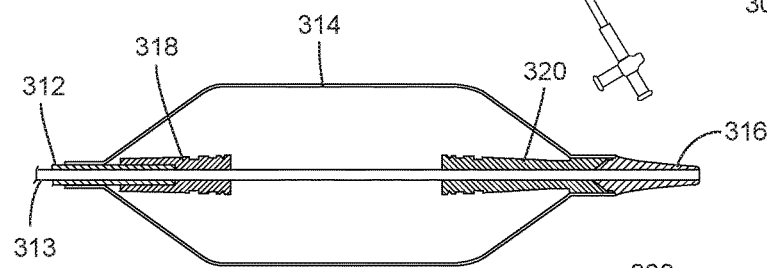
FIG. 33 is an enlarged, cross-sectional view of the distal end portion of the delivery apparatus of FIG. 32.

As best shown in FIG. 33, a pusher element, or stop member, 318 is mounted on the shaft 312 within the proximal portion of the balloon and the nose cone is formed with a stop member 320 that extends into the distal portion of the balloon. The spacing between the distal end of the pusher element 318 and the proximal end of the stop member 320 defines an annular space sized to partially receive a prosthetic valve that is crimped on the balloon. In use, the prosthetic valve is crimped onto the balloon between the pusher element 318 and the stop member 320 such that the proximal end of the prosthetic valve can abut the pusher element and the distal end of the prosthetic valve can abut the stop member (depicted in the embodiment shown in FIG. 47A). In this manner, these two elements assist in retaining the position of the prosthetic valve on the balloon as it is inserted through the introducer 304.

Figure 34:
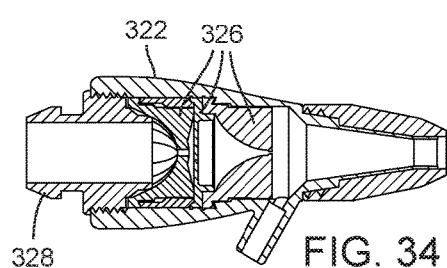
FIG. 34 is a cross-sectional view of the introducer of FIG. 32.
Figure 35:
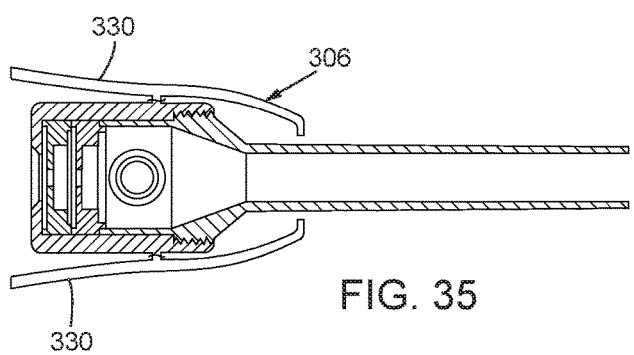
FIG. 35 is a cross-sectional view of the loader of FIG. 32.

As shown in FIG. 32, the introducer 304 comprises an introducer housing 322 and a distal sheath 324 extending from the housing 322. The introducer 304 is used introduce or insert the balloon catheter 302 into a patient's body. As shown in FIG. 34, the introducer housing 322 houses one or more valves 326 and includes a proximal cap 328 for mounting the loader. The loader 306 provides a coupling between the balloon catheter and the introducer. The loader 306 includes two retaining arms 330 that engage the proximal cap 328 of the introducer. The manner of using a loader to assist in inserting a balloon catheter and prosthetic valve into an introducer is described below with respect to the embodiment shown in FIGS. 51-53.

Figure 39:
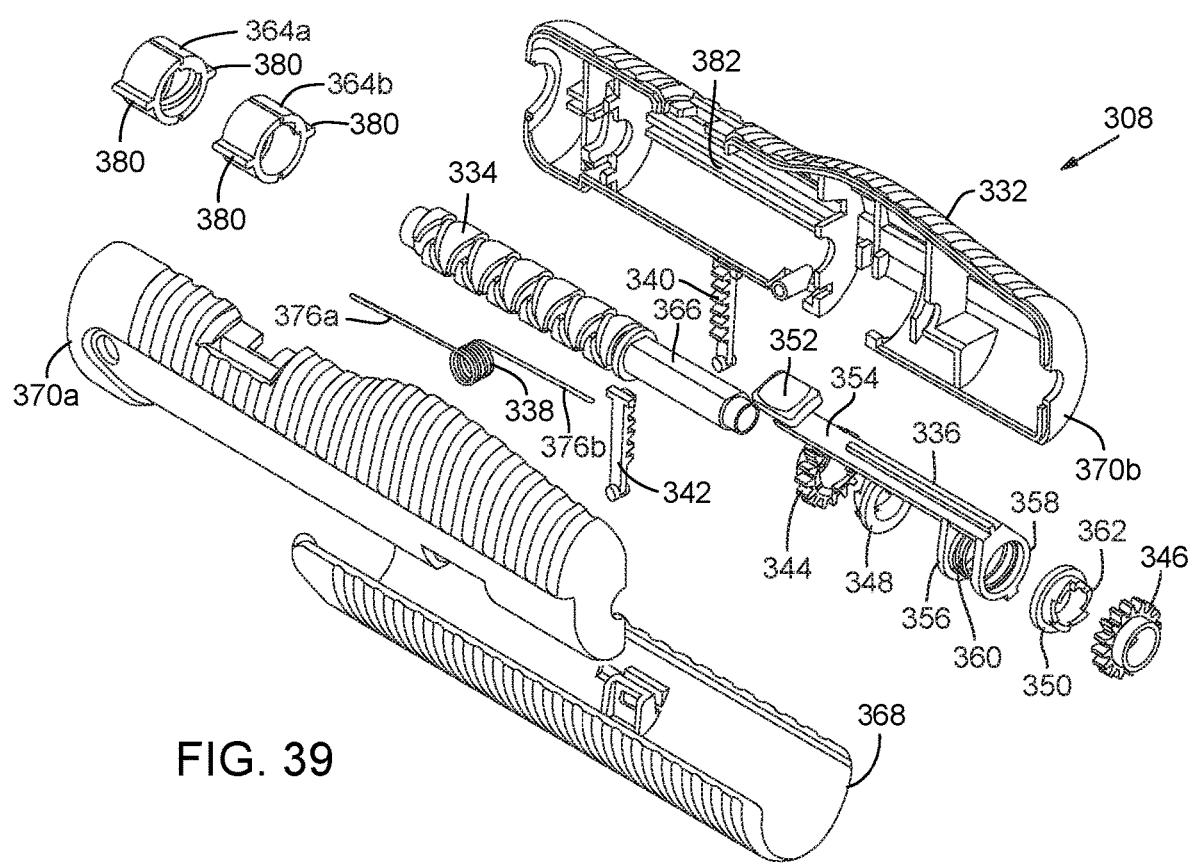
FIG. 39 is an exploded, perspective view of the handle of FIG. 36.

The construction of the handle 308 is shown in FIGS. 36-39. The handle 308 includes a housing 332, which houses a mechanism for effecting controlled deflection, or articulation, of balloon catheter shaft 312. The mechanism in the illustrated embodiment comprises a shaft 334, a sliding mechanism 336, a spring 338, and proximal and distal rack gears 340, 342, respectively. The proximal end portion of the shaft 334 is formed with external threads that engage internal threads of two threaded nuts 364a, 364b inside the handle. The shaft 334 can rotate within the handle but is restricted from translational movement within the handle. The nuts 364 desirably have opposite threads and are disposed on respective portions of the shaft 334 that have corresponding external threads. For example, the proximal nut 364a can have left-handed threads and is disposed on left-handed threads on the shaft, while the distal nut 364b can have right-handed threads and is disposed on right-handed threads on the shaft. This causes the nuts 364 to translate in opposite directions along the threads of the shaft 334 upon its rotation. As best shown in FIG. 39, each nut 364 has a pair of radially extending flanges 380 on diametrically opposite sides of the nut. The inside of the housing is formed with a pair of elongated slots 382 (one of which is shown in FIG. 39) on opposing inside surfaces of the housing. The opposing flanges 380 on each nut 364 can extend into respective slots 382, which prevent rotation of the nuts upon rotation of the shaft 334. In this manner, the nuts 364 are caused to move lengthwise of the shaft 334 upon its rotation.

The distal end portion of the shaft 334 supports a proximal spur gear 344, a distal spur gear 346, a proximal clutch 348, and a distal clutch 350. The shaft 334 has a flat 366 that engages corresponding flats on center bores of the clutches 348, 350, which provides for rotation of the shaft when one of the clutches is engaged and rotated by a respective spur gear, as described below. The sliding mechanism 336 includes a user-engageable actuator 352, an elongate arm 354 extending from actuator 352, and proximal and distal rings 356, 358, respectively, mounted on the distal end portion of the arm 354. Mounted on the shaft 334 and held between the rings is a coil spring 360.

Two pull wires (not shown) extend from the handle through the balloon catheter shaft 312 on diametrically opposite sides of the balloon catheter shaft to its distal end portion. A first pull wire has a proximal end secured to the proximal nut 364a inside the handle and a distal end that is secured to the distal end portion of the balloon catheter shaft 312. A second pull wire has a proximal end secured to the distal nut 364b inside the handle and a distal end that is secured to the distal end portion of the balloon catheter shaft 312 on a diametrically opposite side from the securement location of the first pull wire.

Figure 36:
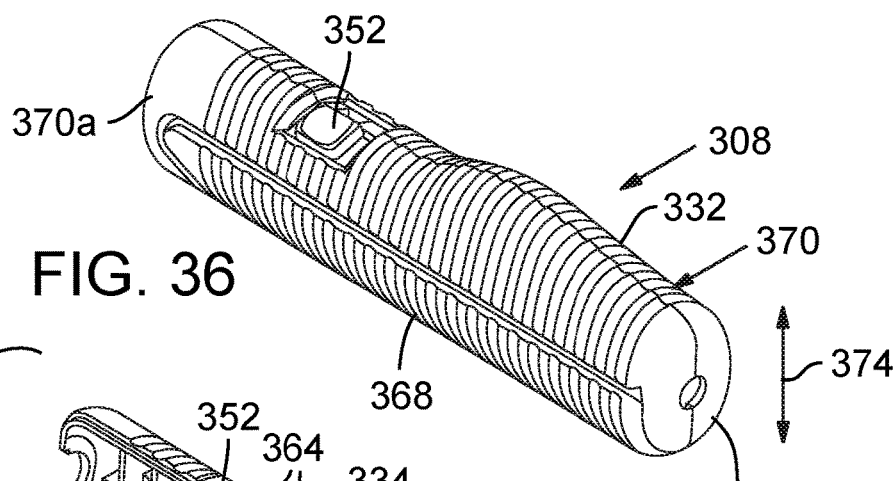
FIG. 36 is a perspective view of the handle of the delivery apparatus shown in FIG. 32.
Figure 37:
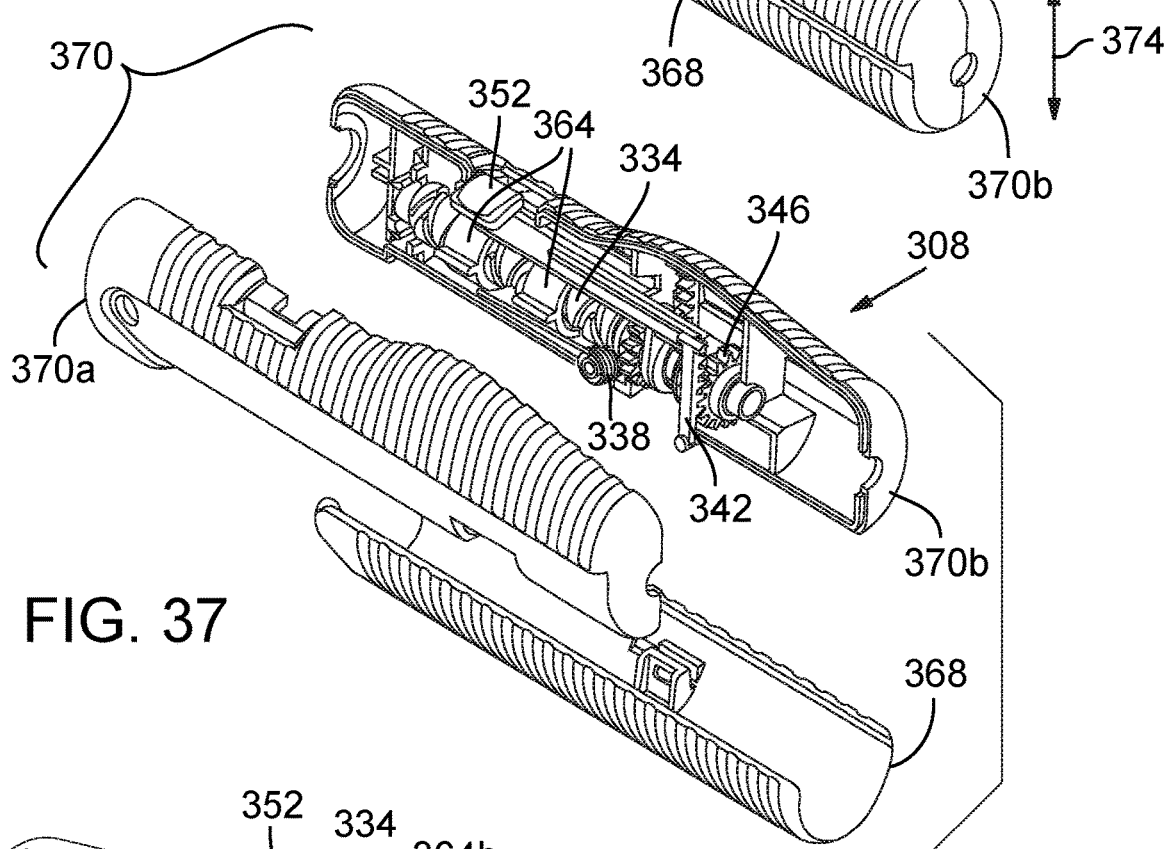
FIG. 37 is a partially exploded, perspective view of the handle of FIG. 36.
Figure 38:
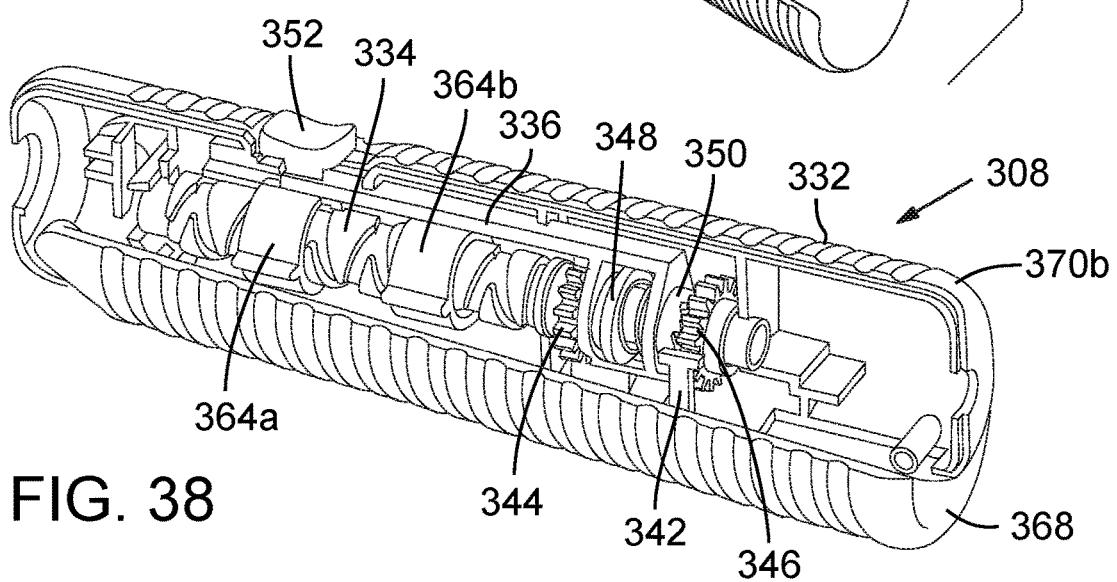
FIG. 38 is a perspective view of the handle of FIG. 36, shown with a portion of the outer housing cut away for purposes of illustration.

The housing 332 is configured to actuate the deflection (articulation) mechanism inside the handle when it is squeezed by the hand of a user. For example, the housing 332 can comprise a lower housing section 368 and an upper housing section 370, which can be comprised of two separable housing sections 370a, 370b for ease of assembly. Referring to FIG. 36, the lower housing section 368 is mounted to the upper housing section 370 in a manner that permits the two sections to move toward and apart from each other a limited distance when squeezed by a user's hand, as indicated by arrow 374. The torsion spring 338 has one arm 376a that bears against the inner surface of the upper housing portion 370 and another arm 376b that bears against the inner surface of the lower housing portion 368 to resiliently urge the two housing portions apart from each other. As such, squeezing the handle moves the upper and lower housing portions together and releasing manual pressure allows the housing portions to move apart from each other a limited amount under the spring force. In an alternative embodiment, a portion of the housing can be made of a flexible or deformable material that can deform when squeezed by the hand of a user in order to actuate the deflection mechanism.

The deflection mechanism works in the following manner. Squeezing the handle 332 causes the rack gears 340, 342 to move in opposite directions perpendicular to shaft 334 (due to movement of the upper and lower housing sections), which in turn causes rotation of the corresponding spur gears 344, 346 in opposite directions. The sliding mechanism 336 can be manually moved between a proximal position, a neutral (intermediate) position, and a distal position. When the sliding mechanism is in the neutral position (FIG. 36), the clutches are disengaged from their respective spur gears, such that rotation of the spur gears does not rotate the shaft 334. However, sliding the sliding mechanism 336 distally to a distal position pushes the coil spring 360 against the distal clutch 350 to engage the distal spur gear 346. While the sliding mechanism is held in the distal position, the handle is squeezed and the resulting rotation of the distal spur gear 346 is transmitted to the shaft 334 to rotate in the same direction, which in turn causes the nuts 364 to move in opposite directions along the shaft 334 (e.g., toward each other). Translation of the nuts 364 in opposite directions applies tension to the first pull wire and introduces slack to the second pull wire, causing the balloon catheter shaft 312 to bend or deflect in a first direction. The face of the clutch 350 that engages spur gear 346 is formed with teeth 362 that cooperate with corresponding features of the gear to rotate the clutch and shaft 334 when the handle is squeezed, and allow the gear to spin or rotate relative to the clutch when manual pressure is removed from the handle. In this manner, the balloon catheter shaft bends a predetermined amount corresponding to each squeeze of the handle. The deflection of the balloon catheter shaft can be controlled by repeatedly squeezing the handle until the desired degree of deflection is achieved.

The balloon catheter shaft 312 can be deflected in a second direction, opposite the first direction by sliding the sliding mechanism 336 in the proximal direction, which pushes the coil spring 360 against the proximal clutch 348 to engage the proximal spur gear 344. While holding the sliding mechanism in the proximal position and squeezing the handle, the proximal spur gear 344 rotates the proximal clutch 348 in the same direction. Rotation of the proximal clutch is transmitted to the shaft 334 to rotate in the same direction, resulting in translation of the nuts 364 in opposite directions (e.g., if the nuts move toward each other when the sliding mechanism is in the distal position, then the nuts move away from each other when the sliding mechanism is in the proximal position). The proximal clutch 348 is similarly formed with teeth 362 that engage the proximal spur gear 344 and cause rotation of the proximal clutch and shaft 334 only when the handle is squeezed but not when manually pressure is removed from the handle. In any case, movement of the threaded nuts 364 applies tension to the second pull wire and introduces slack to the first pull wire, causing the balloon catheter shaft 312 to bend in the opposite direction.

FIGS. 40-42 show an alternative embodiment of a handle, indicated at 400, that can be incorporated in the balloon catheter 302 (in place of handle 308). The handle 400 comprises a housing 402, which can be formed from two halves 402a, 402b for ease of assembly. Two wheels, or rotatable knobs, 404a, 404b are positioned on opposite sides of the handle. The knobs are mounted on opposite ends of a shaft 406 having gear teeth 408. A rotatable, hollow cylinder 410 extends lengthwise inside of the handle in a direction perpendicular to shaft 406. The cylinder 410 includes external gear teeth 412 that engage the gear teeth 408 on shaft 406. The inner surface of the cylinder 410 is formed with internal threads 414, which can include right-handed and left-handed threads. A proximal threaded nut 416a and a distal threaded nut 416b are disposed inside of the cylinder 410 and are mounted for sliding movement on a rail 418 that extends co-axially through the cylinder. The nuts 416a, 416b have external threads that are threaded in opposite directions and engage the corresponding right-handed and left-handed threads on the inner surface of the cylinder 410. The rail 418 has a flat 420 that engages corresponding flats on the inner bores of the nuts 416a, 416b, which allows the nuts to translate along the length of the rail without rotating.

First and second pull wires (not shown) are provided and secured to respective nuts 416a, 416b and the distal end of the balloon catheter shaft 312 as previously described. Deflection of the balloon catheter shaft 312 in first and second opposing directions can be accomplished by rotating the knobs 404a, 404b (which rotate together) clockwise and counterclockwise. For example, rotating the knobs clockwise produces rotation of the cylinder 410 via gear teeth 408 engaging gear teeth 412. Rotation of cylinder 410 causes the nuts 416a, 416b to move in opposite directions along the rail 418 (e.g., toward each other). Translation of the nuts in opposite directions applies tension to the first pull wire and introduces slack to the second pull wire, causing the balloon catheter shaft 312 to bend or deflect in a first direction. Rotating the knobs counterclockwise produces rotation of the cylinder 410 in a direction opposite its initial rotation mentioned above. Rotation of cylinder 410 causes the nuts 416a, 416b to move in opposite directions along the rail 418 (e.g., away each other). Translation of the nuts in opposite directions applies tension to the second pull wire and introduces slack to the first pull wire, causing the balloon catheter shaft 312 to bend or deflect in a second direction, opposite the first direction.

The handle 400 can optional include a pusher actuation mechanism 422 that is configured to move a pusher device adjacent the distal end of the balloon catheter. The pusher device extends partially over the balloon and holds the prosthetic valve in place on the balloon as the prosthetic valve and balloon catheter are inserted through the introducer. A pusher device is disclosed in co-pending application Ser. No. 12/385,555, which is incorporated herein by reference. The actuation mechanism 422 is pivotably connected to a linkage arm 424, which in turn is pivotably connected to a proximal holder 426 of the pusher device (not shown). The pusher device can extend from the proximal holder 426 to the balloon 314. Moving the actuation mechanism 422 to a distal position moves the pusher device in a position partially extending over the balloon 314 and holding the prosthetic valve in place on the balloon for insertion through the introducer 304. Moving the actuation mechanism 422 to a proximal position moves the pusher device proximally away from the balloon and the prosthetic valve once inside the heart so that the balloon can be inflated for deployment of the prosthetic valve. If a movable pusher device is not used (as in the illustrated balloon catheter 302), then the pusher actuation mechanism 422 would not be needed. For example, in lieu of or in addition to such a pusher device, stop members 318, 320 inside the balloon can be used to retain the position of the prosthetic valve on the balloon (FIGS. 33 and 47A).

Figure 43:
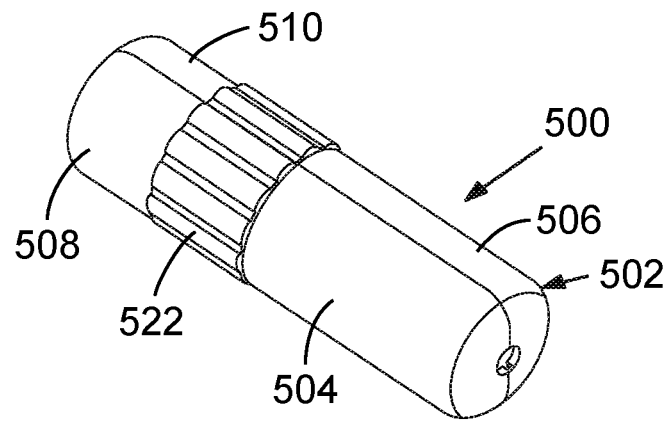
FIG. 43 is a perspective view of another embodiment of a handle that can be used in the delivery apparatus of FIG. 32.
Figure 44:
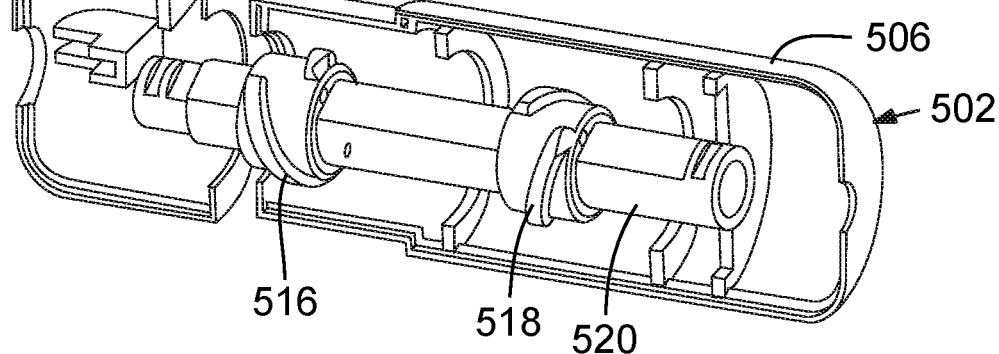
FIG. 44 is a perspective view of the handle of FIG. 43, with a portion of the outer housing and some internal components removed for purposes of illustration.
Figure 45:
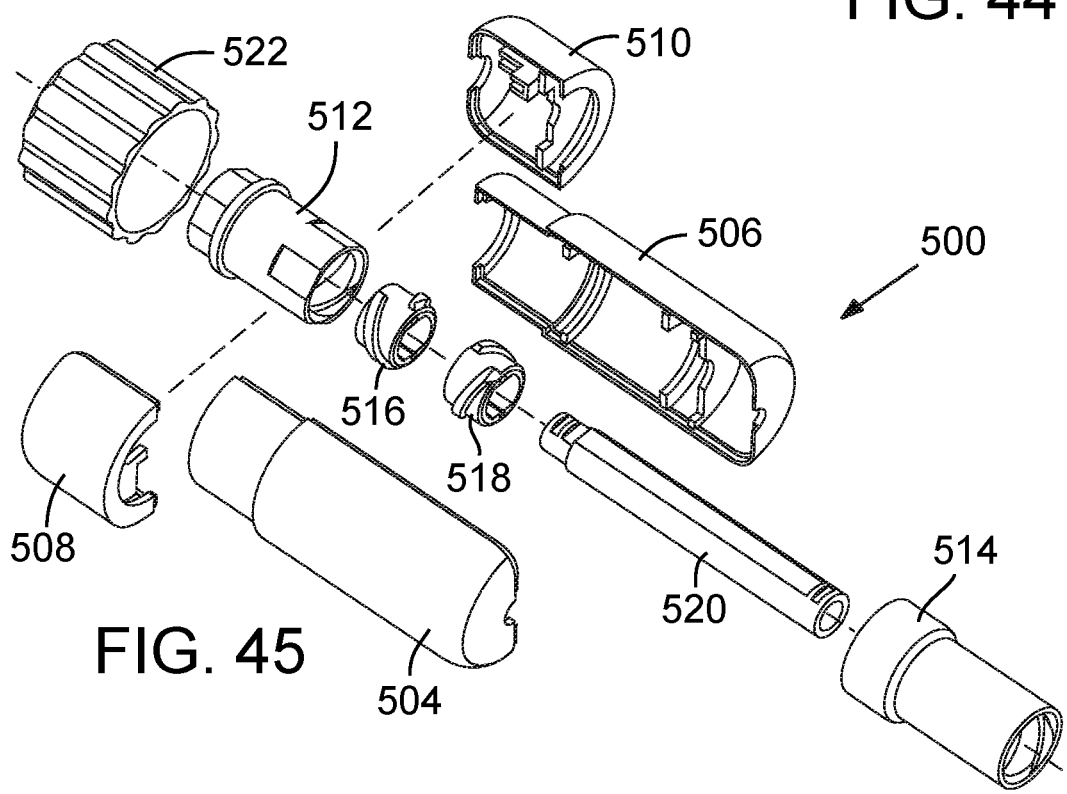
FIG. 45 is an exploded, perspective view of the handle of FIG. 43.

FIGS. 43-45 show another embodiment of a handle, indicated at 500, that can be incorporated in the balloon catheter 302 (in place of handle 308). The handle 500 comprises a housing 502, which can be formed from multiple housing sections, including first and second distal housing portions 504, 506, respectively, that form a distal housing space, and first and second proximal housing portions 508, 510, respectively, that form a proximal housing space. The housing houses a proximal cylinder 512 and a distal cylinder 514, which house proximal and distal nuts 516, 518, respectively. The nuts are disposed on a rail 520 that extends co-axially through the cylinders 512, 514. The cylinders 512, 514 have opposing internal threads, e.g., the proximal cylinder can have right-handed threads and the distal cylinder can have left-handed threads. The cylinders 512, 514 are secured to each other end-to-end (e.g., with a frictional fit between the distal end of the proximal cylinder and the proximal end of the distal cylinder) so that both rotate together. In other embodiments, the cylinders 512, 514 can be formed as a single cylinder having left-handed and right-handed threads as used in the handle 400 described above.

A user-engageable, rotatable knob 522 is mounted on the outside of the housing 502 and engages the proximal cylinder 512 (e.g., through an annular gap in the housing) such that rotation of the knob 522 causes corresponding rotation of the cylinders 512, 514. The deflection mechanism of this embodiment works in a manner similar to that shown in FIGS. 40-42 to alternatively apply tension and introduce slack in first and second pull wires (not shown) secured to the nuts 516, 518, respectively. For example, rotating the knob 522 in a first direction causes the nuts to translate in opposite directions along the rail 520 (e.g., toward each other), which is effective to apply tension to the first pull wire and introduce slack to the second pull wire, causing the balloon catheter shaft 312 to bend or deflect in a first direction. Rotating the knob 522 in a second direction causes the nuts to translate in opposite directions (e.g., away from each other), which is effective to apply tension to the second pull wire and introduce slack to the first pull wire, causing the balloon catheter shaft 312 to bend or deflect in a second direction, opposite the first bending direction.

Figure 46:
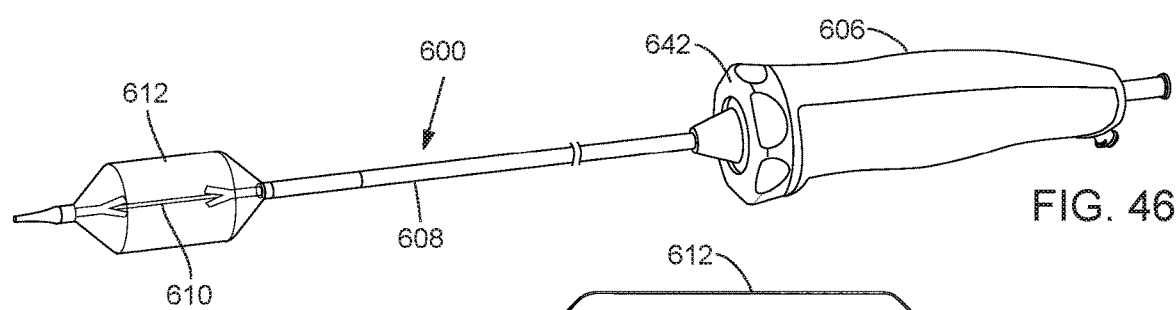
FIG. 46 is a perspective view of a delivery apparatus for a prosthetic heart valve, according to another embodiment.
Figure 50:
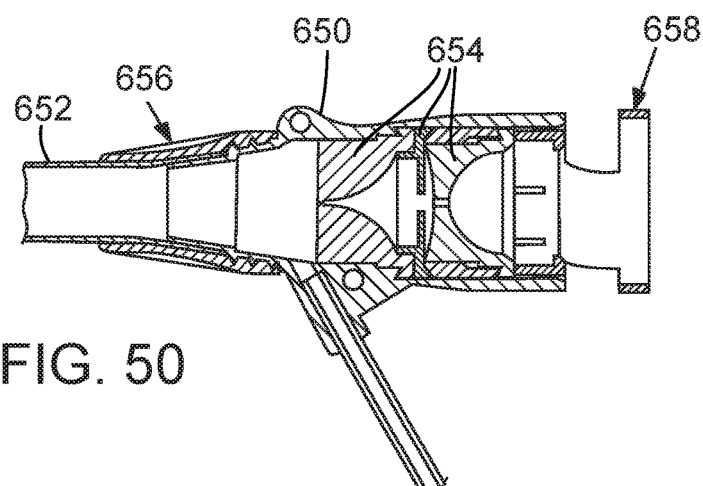
FIG. 50 is an enlarged, cross-sectional view of the proximal housing portion of the introducer shown in FIG. 49.
Figure 51:
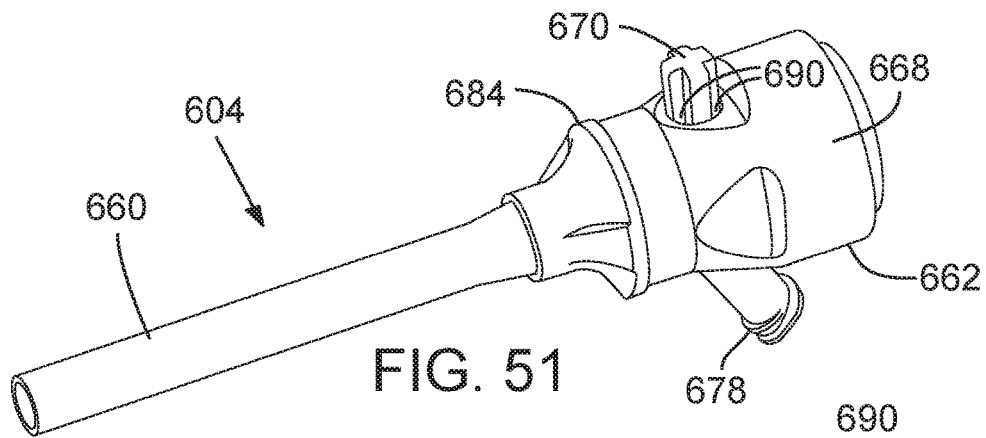
FIG. 51 is a perspective view of a loader, according to another embodiment.
Figure 52:
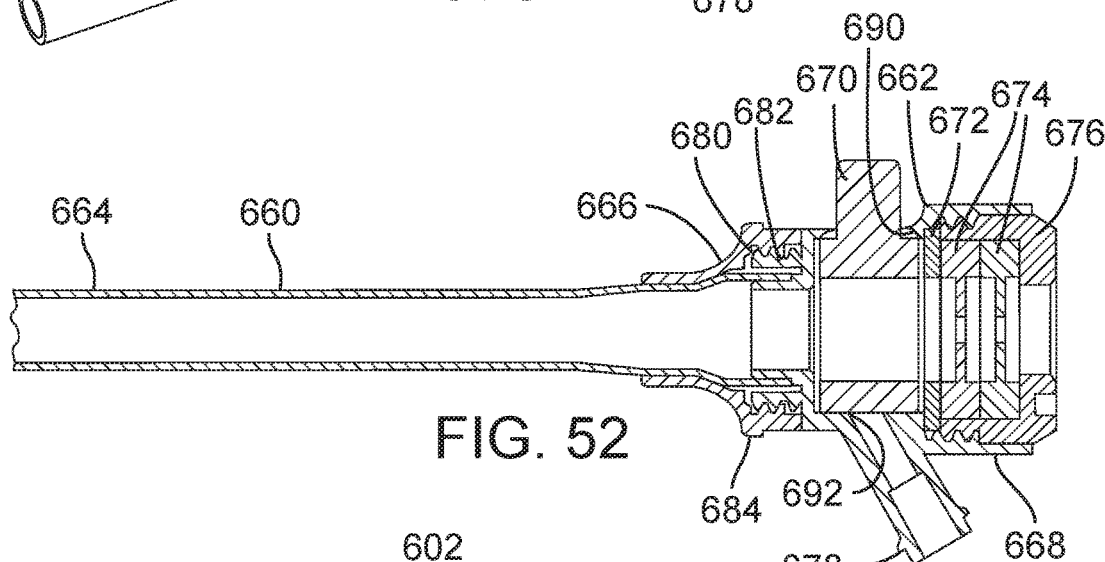
FIG. 52 is a cross-sectional view of the loader shown in FIG. 51.

FIG. 46 discloses a delivery apparatus 600, according to another embodiment, that can be used to implant an expandable prosthetic heart valve. The delivery apparatus 600 is specifically adapted for use in introducing a prosthetic valve into a heart in a transapical or transaortic procedure. A delivery system for implanting a prosthetic heart valve can comprise the delivery apparatus 600, an introducer 602 (FIGS. 49-50), and a loader 604 (FIGS. 51-52).

Figure 47:
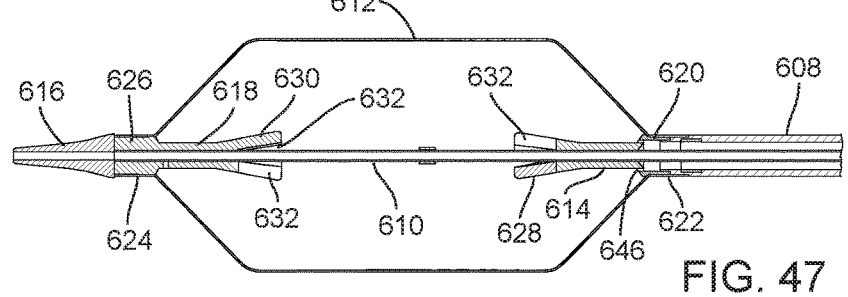
FIG. 47 is an enlarged, cross-sectional view of the distal end portion of the delivery apparatus of FIG. 46.
Figure 47A:
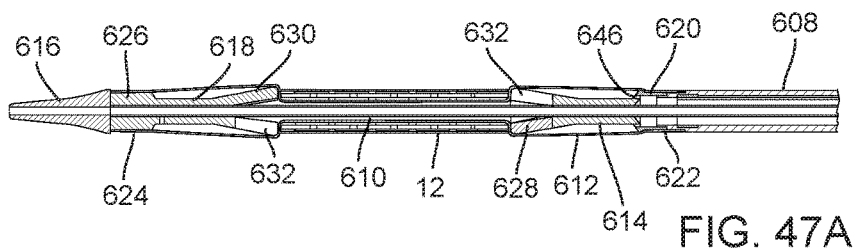
FIG. 47A is an enlarged, cross-sectional view of the distal end portion of the delivery apparatus of FIG. 46 showing a prosthetic heart valve mounted in a crimped state on the balloon of the delivery apparatus.

Referring to FIGS. 46-47, the delivery apparatus 600 in the illustrated form is a balloon catheter comprising a handle 606, a steerable shaft 608 extending from the handle 606, an inner shaft 610 extending from the handle 606 coaxially through the steerable shaft 608, an inflatable balloon 612 extending from the distal end of the steerable shaft 608, a proximal shoulder, or stop member, 614 extending from the distal end of the steerable shaft 608 into the proximal end region of the balloon, a nose cone 616 mounted on the distal end of the inner shaft 610, and a distal shoulder, or stop member, 618 mounted on the inner shaft 610 within the distal end region of the balloon. The distal stop member 618 can be an integral extension of the nose cone 616 as shown. The proximal stop member 614 can have a proximal end portion 620 secured to the outside surface of the distal end portion of the steerable shaft 608. The balloon 612 can have a proximal end portion 622 and a distal end portion 624, with the proximal end portion 622 being secured to the outer surfaces of the shaft 608 and/or the end portion 620 of the proximal stop 614 and the distal end portion 624 being secured to the outer surface of a distal end portion 626 of the distal stop member 618.

As best shown in FIG. 47, the proximal end portion 620 of the proximal stop member 614 includes one or more openings 646 for inflation fluid formed in the annular wall between the outer surface of the inner shaft 610 and the inner surface of the outer shaft 608. The openings 646 allow inflation fluid to flow outwardly from the space between the inner shaft 610 and the outer shaft 608 into the balloon in the distal direction.

The proximal stop member 614 has a distal end portion 628 in form of a substantially cone-shaped member, and the distal stop member 618 has a proximal end portion 630 of the same shape. The spacing between the cone-shaped members 628, 630 defines an annular space sized to at least partially receive a prosthetic valve that is crimped on the balloon. In use, as shown in FIG. 47A, the prosthetic valve 12 is crimped onto the balloon between the cone-shaped members 628, 630 such that the prosthetic valve is retained on the balloon between the cone-shaped members as the prosthetic valve is advanced through the introducer. Desirably, the spacing between the cone-shaped members 628, 630 is selected such that the prosthetic valve is slightly wedged between the cone-shaped members with the non-inflated balloon extending between the proximal end of the prosthetic valve and the proximal member 628 and between the distal end of the prosthetic valve and the distal member 630. In addition, the maximum diameter of the members 628, 630 at their ends adjacent the ends of the prosthetic valve desirably is about the same as or slightly greater than the outer diameter of the frame of the prosthetic valve 12 when crimped onto the balloon.

As further shown in FIG. 47, each of the cone-shaped members 628, 630 desirably is formed with one or more slots 632. In the illustrated embodiment, each of the cone-shaped members 628, 630 has three such slots 632 that are equally angularly spaced in the circumferential direction. The slots 632 facilitate radial compression of the cone-shaped members 628, 630, which is advantageous during manufacturing of the delivery device and during crimping of the prosthetic valve. In particular, the proximal and distal ends 622, 624 of the balloon may be relatively smaller than the maximum diameter of the cone-shaped members 628, 630. Thus, to facilitate insertion of the cone-shaped members 628, 630 into the balloon during the assembly process, they can be radially compressed to a smaller diameter for insertion into the balloon and then allowed to expand once inside the balloon. When the prosthetic valve is crimped onto the balloon, the inside surfaces of the crimping device (such as the surfaces of crimping jaws) may contact the cone-shaped members 628, 630 and therefore will radially compress the cone-shaped members along with the prosthetic valve. Typically, the prosthetic valve will undergo a small amount of recoil (radial expansion) once removed from the crimping device. Due to the compressibility cone-shaped members 628, 630, the prosthetic valve can be fully compressed to a crimped state in which the metal frame of the prosthetic valve has an outer diameter equal to or less than the maximum diameter of the cone-shaped members (accounting for recoil of the prosthetic valve).

The slots 632 in the cone-shaped members 628, 630 also allow inflation fluid to flow radially inwardly through the cone-shaped members and through the region of the balloon extending through the crimped prosthetic valve in order to facilitate expansion of the balloon. Thus, inflation fluid can flow from a proximal region of the balloon, inwardly though slots 632 in proximal stop member 628, through the region of the balloon extending through the prosthetic valve, outwardly through slots 632 in distal stop 630, and into a distal region of the balloon. Another advantage of the distal stop member 618 is that it serves a transition region between the nose cone and the prosthetic valve. Thus, when the prosthetic valve is advanced through the leaflets of a native valve, the distal stop member 618 shields the distal end of the prosthetic valve from contacting the surrounding tissue, which can otherwise dislodge or prevent accurate positioning of the prosthetic valve prior to deployment.

Figure 48:
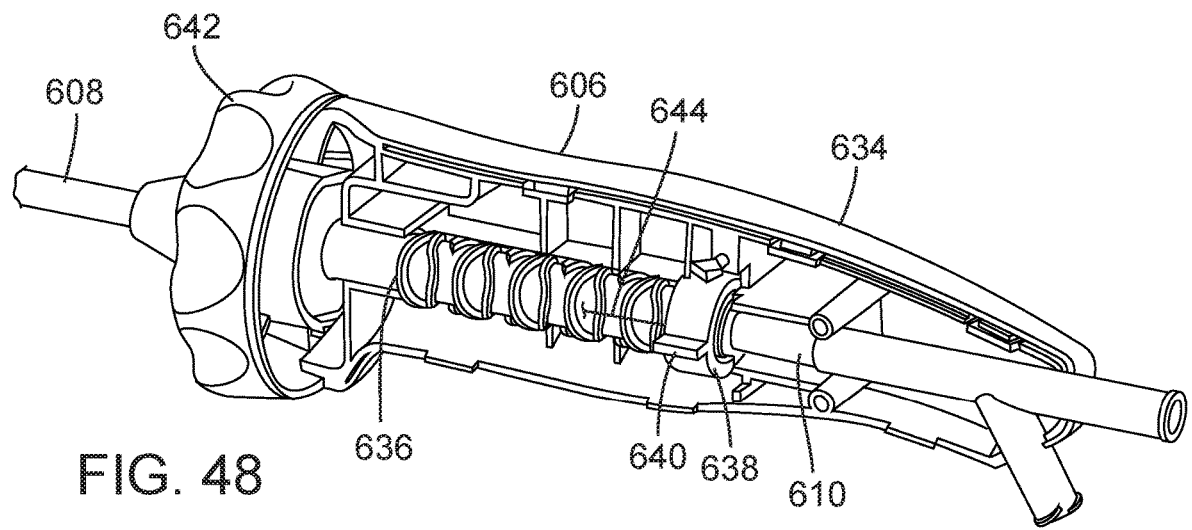
FIG. 48 is a perspective view of the handle of the delivery apparatus of FIG. 46, with a portion of the outer housing removed for purposes of illustration.

The construction of the handle 606 is shown in FIG. 48. The handle 606 comprises a housing 634, which can be formed from multiple housing sections. The housing 634 houses a mechanism for effecting controlled articulation/deflection of the shaft 608. The mechanism in the illustrated embodiment comprises a threaded shaft 636, and a threaded nut 638 disposed on the shaft. The proximal end portion of the shaft 636 is formed with external threads that engage internal threads of the threaded nut 638. The shaft 636 can rotate within the handle but is restricted from translational movement within the handle. The nut 638 has opposing flanges 640 (one of which is shown in FIG. 48), which extend into respective slots formed on the inside surfaces of the housing to prevent rotation of the nut. In this manner, the nut 638 translates along the threads of the shaft 636 upon rotation of the shaft.

The distal end portion of the shaft 636 supports user-engageable, rotatable knob 642. The shaft 636 is coupled to the knob 12 such that rotation of the knob causes corresponding rotation of the shaft 636. A pull wire 644 extends from the handle through the balloon catheter shaft 608 on one side of the balloon catheter shaft to its distal end portion. The pull wire 644 has a proximal end secured to the threaded nut 638 inside the handle and a distal end that is secured to the distal end portion of the balloon catheter shaft 608. The articulation mechanism of this embodiment works by rotating the knob 642 in one direction, which causes the threaded nut 638 to translate along the shaft 636, which is effective to apply tension to the pull wire causing the balloon catheter shaft 608 to bend or articulate in a predetermined direction. Rotating the knob 642 in the opposite direction causes to the nut 638 to translate in the opposite direction, thereby releasing tension in the pull wire, which allows the shaft 608 to deflect in the opposite direction under its own resiliency. In alternative embodiments, another threaded nut and respective pull wire can be provided in the housing to allow for bi-directional steering of the shaft 608, as described above in connection with the embodiments of FIGS. 36-45.

Figure 49:
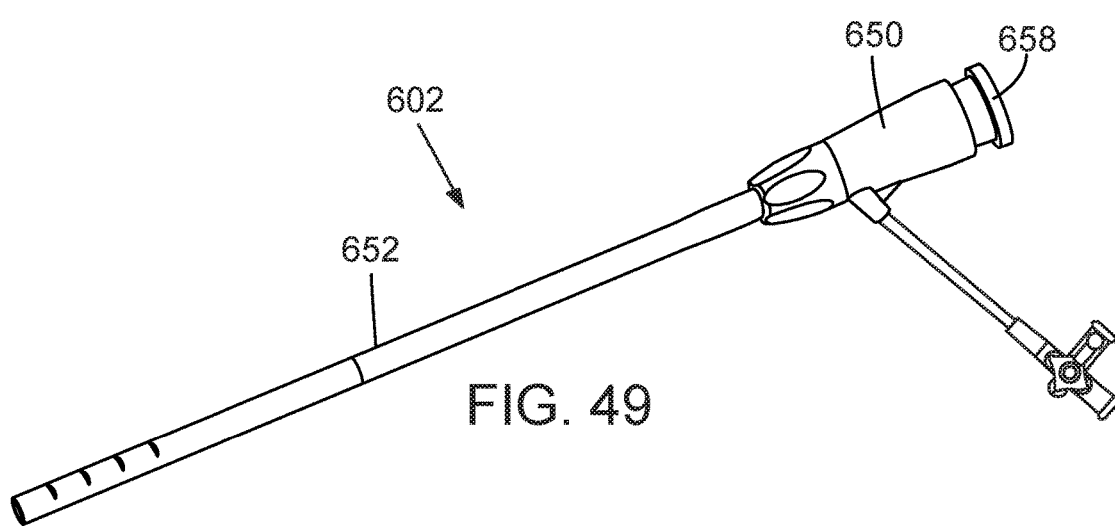
FIG. 49 is a perspective view of an introducer, according to another embodiment.

FIG. 49 is a perspective view of the introducer 602, which comprises an introducer housing assembly 650 and a sheath 652 extending from the housing assembly 650. The introducer 602 is used to introduce or insert the delivery apparatus 600 into a patient's body. In a transapical procedure, for example, the sheath 652 is inserted through surgical incisions in the chest and the apex of the heart to position the distal end of the sheath in the left ventricle (such as when replacing the native aortic valve). The introducer 602 serves as a port or entry point for inserting the delivery apparatus into the body with minimal blood loss. As shown in FIG. 50, the introducer housing 650 houses one or more valves 654, and includes a distal cap 656 to secure sheath 652 to the housing 650 and a proximal cap 658 for mounting the loader 604.

FIGS. 51-52 are respective and cross-sectional views of the loader 604, which is used to protect the crimped prosthesis during insertion into the introducer 602. The loader 604 in the illustrated configuration comprises a distal loader assembly 660 and a proximal loader assembly 662. The distal loader assembly 660 and proximal loader assembly 662 can be secured to each other by mating female and male threads 680 and 682, respectively. The distal loader assembly 660 comprises a loader tube 664 and a loader distal cap 666. The proximal loader assembly 662 comprises a loader housing 668, a button valve 670, a washer 672, two disc valves 674, and a proximal loader cap 676. The distal loader cap 666 can be formed with a lip 684 that is configured to engage the proximal cap 658 of the introducer 602 as shown in FIG. 53.

In use, the proximal loader assembly 662 (apart from the distal loader assembly 660) can be placed on the balloon catheter shaft 608 prior to placing the prosthetic valve on the balloon and the crimping the prosthetic valve to avoid passing the crimped prosthetic valve through the sealing members 674 inside the housing 668. After the prosthetic valve is crimped onto the balloon, the distal loader assembly 660 is slid over the crimped prosthetic valve and secured to the proximal loader assembly 662 (by screwing threads 682 into threads 680). As shown in FIG. 53, the loader tube 664 (while covering the crimped prosthetic valve) can then be inserted into and through the introducer housing 650 so as to extend through the internal sealing members 654 (FIG. 50). The loader tube 664 therefore prevents direct contact between the sealing members 654 of the introducer and the crimped prosthetic valve. The loader 604 can be secured to the introducer 602 by pressing the annular lip 684 of the loader into the proximal cap 658 of the introducer. After insertion of the loader tube into the introducer, the prosthetic valve can be advanced from the loader tube, through the sheath 652, and into a region with the patient's body (e.g., the left ventricle).

Figures 53, 54, 55:
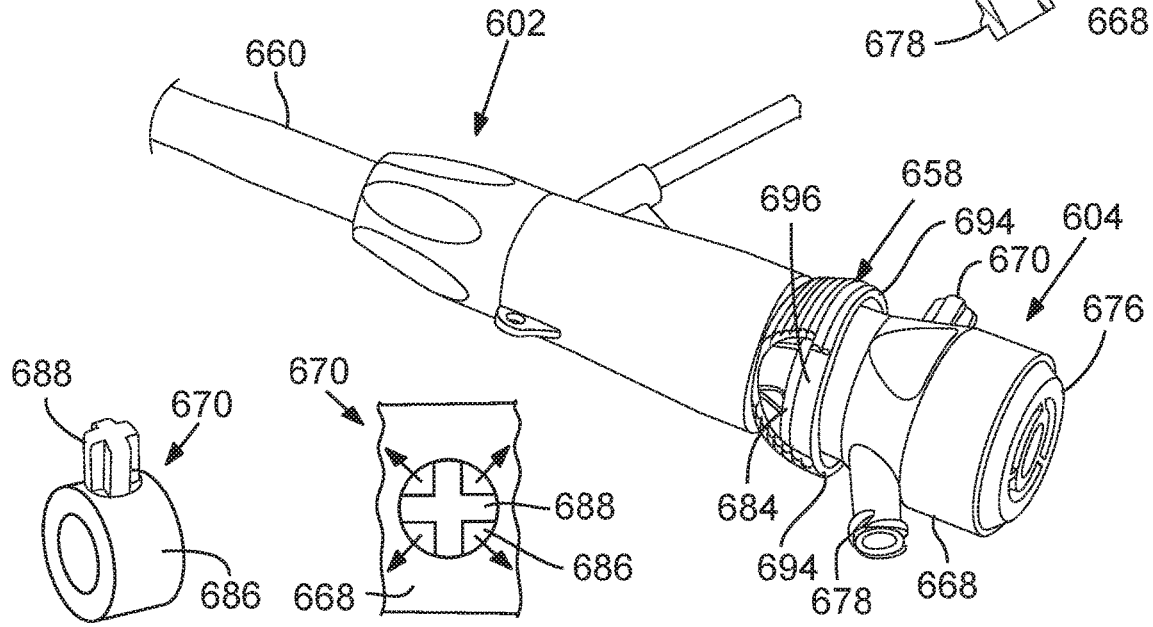
FIG. 53 is a perspective view of the loader of FIG. 51 shown inserted into the introducer of FIG. 49.
FIG. 54 is a perspective view of the button valve of the loader shown in FIG. 51.
FIG. 55 is a top plan view of the button valve shown in FIG. 51.

As best shown in FIG. 53, the proximal cap 658 of the introducer comprises first and second diametrically opposed ribbed portions 694 and first and second diametrically opposed, deflectable engaging portions 696 extending between respective ends of the ribbed portions. When the loader 604 is inserted into the introducer 602, the lip 684 of the loader snaps into place on the distal side of the engaging portions 696, which hold the loader in place relative to the introducer. In their non-deflected state, the ribbed portions 694 are spaced slightly from the adjacent surfaces of the cap 666 of the loader. To remove the loader from the introducer, the ribbed portions 694 are pressed radially inwardly, which causes the engaging portions 696 to deflect outwardly beyond the lip 684, allowing the loader and the introducer to be separated from each other.

Fluid (e.g., saline) can be injected into the loader 604 through a lured port 678, which when pressurized by fluid will allow for fluid flow in a single direction into the loader housing. Alternatively, fluid (e.g., blood, air and/or saline) can be removed from the loader 604 by depressing the crossed portion of the button valve 670, which creates an opening between the valve 670 and the loader housing. As best shown in FIGS. 52 and 54, the button 670 in the illustrated embodiment comprises an elastomeric annular ring 686 and a user-engageable projection 688 that extends outwardly through an opening 690 in the loader housing 668. The ring 686 seals the opening 690 and another opening 692 in the loader housing that communicates with the port 678. When a pressurized fluid is introduced into the port 678, the pressure of the fluid causes the adjacent portion of the ring 686 to deflect inwardly and away from its position sealing opening 692, allowing the fluid to flow into the loader. Alternatively, to remove fluid from the loader, a user can depress projection 688, which causes the adjacent portion of the ring 686 to deflect inwardly and away from its position sealing the opening 690, allowing fluid in the loader to flow outwardly through the opening 690.

General Considerations

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods. As used herein, the terms "a", "an" and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A," "B," "C," "A and B," "A and C," "B and C" or "A, B and C."

As used herein, the term "coupled" generally means physically coupled or linked and does not exclude the presence of intermediate elements between the coupled items absent specific contrary language.

In view of the many possible embodiments to which the principles of the disclosed technology may be applied, it should be recognized that the illustrated embodiments are only preferred examples and should not be taken as limiting the scope of the disclosure. Rather, the scope of the disclo-

The invention claimed is:

1. A delivery device for implantation of a prosthetic heart valve within a heart, the prosthetic heart valve being radially expandable from a radially compressed state to a radially expanded state, the delivery device comprising:
    a catheter;
    an inflatable balloon position at a distal portion of the catheter; and
    a proximal stop and a distal stop coupled to the catheter and configured to limit longitudinal movement of the prosthetic heart valve relative to the balloon while the prosthetic heart valve is mounted over the balloon in the radially compressed state between the proximal stop and the distal stop;
    wherein the proximal stop and the distal stop are at least partially positioned within the balloon and configured to be positioned adjacent a respective end of the prosthetic heart valve when the prosthetic heart valve is radially compressed between the proximal and distal stops;
    wherein the proximal and distal stops each comprise at least one passageway that allows balloon inflation fluid to flow radially inwardly or radially outwardly through the proximal and distal stops; and
    wherein the proximal stop and the distal stop each comprises a base portion coupled to the catheter and a plurality of prongs extending from the base portion, the plurality of prongs being separated by the at least one passageway, wherein each of the plurality of prongs extends axially and radially outwardly from the respective base portion to a free end, and wherein the free ends of the prongs are disconnected from one another other than via the base portion.

2. The delivery device of claim 1, wherein the passageways of the proximal and distal stops allow the proximal and distal stops to be radially compressed to a smaller diameter.

3. The delivery device of claim 1, wherein the at least one passageway comprises at least one longitudinally extending slot in each of the proximal and distal stops.

4. The delivery device of claim 1, wherein, when the prosthetic heart valve is mounted on the delivery device in the radially compressed state, the proximal stop and the distal stop are configured to allow the balloon-inflation fluid to flow from a proximal portion of the balloon, through the at least one passageway in the proximal stop, through an intermediate portion of the balloon positioned within the prosthetic heart valve, through the at least one passageway in the distal stop, and into a distal portion of the balloon.

5. The delivery device of claim 1, wherein a proximal end of the balloon is attached to the proximal stop and a distal end of the balloon is attached to the distal stop.

6. The delivery device of claim 1, wherein the delivery device further comprises an outer shaft having a lumen and an inner shaft extending through the lumen of the outer shaft, wherein the proximal stop is attached to a distal end of the outer shaft and/or attached to an outer surface of the inner shaft, and wherein the distal stop is attached to an outer surface of the inner shaft.

7. The delivery device of claim 6, wherein the proximal stop is attached to the distal end of the outer shaft and further comprises at least one fluid passageway that allows the balloon-inflation fluid to flow through the at least one passageway and into the balloon.

8. The delivery device of claim 1, wherein each of the proximal and distal stops decreases in diameter in a direction extending away from the prosthetic heart valve.

9. The delivery device of claim 1, wherein the delivery device further comprises a nosecone attached to a distal end of the distal stop.

10. The delivery device of claim 1, wherein at least one of the stops comprises at least three longitudinal slots that allow the stop to be radially compressed to a smaller diameter when the prosthetic heart valve is crimped onto the delivery device.

11. The delivery device of claim 1, in combination with a prosthetic heart valve crimped onto the balloon between the proximal and distal stops.

12. The delivery device of claim 1, wherein the at least one passageway in the proximal stop allows the balloon-inflation fluid to flow radially inwardly during inflation and radially outwardly during deflation.

13. The delivery device of claim 1, wherein the at least one passageway in the distal stop allows the balloon-inflation fluid to flow radially outwardly during inflation and radially inwardly during deflation.

14. The delivery device of claim 1, wherein the proximal stop comprises a cone-shaped end portion that includes the plurality of prongs and the at least one passageway of the proximal stop.

15. The delivery device of claim 1, wherein the distal stop comprises a cone-shaped end portion that includes the plurality of prongs and the at least one passageway of the distal stop.

16. The delivery device of claim 1 in combination with a prosthetic heart valve mounted over the balloon between the proximal and distal stops.

17. The combination of claim 16, wherein the prosthetic heart valve comprises a prosthetic aortic valve.

18. The combination of claim 16, wherein the prosthetic heart valve is mounted on over the balloon in a radially compressed configuration.

19. The delivery device of claim 1, wherein a distal end of the balloon is attached to the base portion of the distal stop.

* * * * *